(12) United States Patent
Iris

(10) Patent No.: US 9,315,803 B2
(45) Date of Patent: Apr. 19, 2016

(54) METHOD FOR THE PREPARATION OF MODIFIED BACTERIOPHAGES BY INSERTION OF RANDOM SEQUENCES IN THE TARGETING PROTEINS OF SAID BACTERIOPHAGES

(75) Inventor: François Iris, Chaville (FR)

(73) Assignee: PHERECYDES PHARMA, Paris (FR)

(*) Notice: Subject to any disclaimer, the term of this patent is extended or adjusted under 35 U.S.C. 154(b) by 785 days.

(21) Appl. No.: 12/520,789

(22) PCT Filed: Dec. 18, 2007

(86) PCT No.: PCT/FR2007/002101
§ 371 (c)(1),
(2), (4) Date: Jan. 22, 2010

(87) PCT Pub. No.: WO2008/093009
PCT Pub. Date: Aug. 7, 2008

(65) Prior Publication Data
US 2011/0027231 A1 Feb. 3, 2011

(30) Foreign Application Priority Data
Dec. 20, 2006 (FR) ..................................... 06 55721

(51) Int. Cl.
*C12Q 1/68* (2006.01)
*C12Q 1/70* (2006.01)
*C12N 15/10* (2006.01)

(52) U.S. Cl.
CPC .. *C12N 15/1037* (2013.01); *C12N 2795/10111* (2013.01)

(58) Field of Classification Search
USPC ............................ 435/5, 6.12, 7.2, 235.1, 441
See application file for complete search history.

(56) References Cited

U.S. PATENT DOCUMENTS

| 6,203,986 B1 * | 3/2001 | Singer et al. ................. 435/6.11 |
| 7,632,512 B2 * | 12/2009 | Fairhead .................... 424/234.1 |
| 2003/0216338 A1 | 11/2003 | Merril et al. |

FOREIGN PATENT DOCUMENTS

| EP | 0698091 A | 2/1996 |
| WO | 2006066224 A | 6/2006 |

OTHER PUBLICATIONS

Cadwell et al., Genome Res. 1992. 2: 28-33 Randomization of genes by PCR mutagenesis.*
Miller et al., Microbiol. Mol. Biol. Rev. 2003, 67(1):86. Bacteriophage T4 Genome.*
Iwamoto et al Domains near ATP gamma phosphate in the catalytic site of H—ATPase. Model proposed from mutagenesis and inhibitor studies Feb. 15, 1993 The Journal of Biological Chemistry, 268, 3156-3160.*
Ngo, in the Protein Folding Problem and Tertiary Structure Prediction, Merz et al. (eds.), Birkhauser Boston: Boston, MA, pp. 433 and 492-495, 1994.*
Skolnick et al., From genes to protein structure and function: novel applications of computational approaches in the genomic era TIBTECH Jan. 2000 (vol. 18) pp. 34-39.*
Kimchi-Sarfaty Cet al., A "silent" polymorphism in the MDR1 gene changes substrate specificity.Science. Jan. 26, 2007;315(5811):525-8.*
Pouillot et al., Genetically Engineered Virulent Phage Banks in the Detection and Control of Emergent Pathogenic BacteriaBiodefense Strategy, Practice, and Science. Jun. 2010, 8(2): 155-169.*
Bredo, et al.,"Gene Reconstitution Using High Efficiency Homologous Recombination Between a Bacteriophage FD and a Plasmid," Journal of Biotechnology, 2006, pp. 286-290, vol. 126 No. 3, Elsevier Science Publishers, Amsterdam, NL.
Yoichi, et al.,"Alteration of Tail Fiber Protein GP38 Enables T2 Phage to Infect *Escherichia coli* 0157:H7," Journal of Biotechnology, 2005, pp. 101-107, vol. 115 No. 1, Elsevier Science Publishers, Amsterdam, NL.
Switala-Jelen, et al."Mutations in Bacteriophage T4 Genome," Acta Virologica, 2002, pp. 57-62, vol. 46 No. 2, Academia Prague, Prague, CS.
Desplats et al."The Diversity and Evolution of the T4-Type Bacteriophages," Research in Microbiology, 2003, pp. 259-267, vol. 154 No. 4.
Tetart et al.,"Genome Plasticity in the Distal Tail Fiber Locus of the T-Even Bacteriophage: Recombination Between Conserved Motifs Swaps Adhesin Specificity," Journal of Molecular Biology, 1998, pp. 543-556, vol. 282 No. 3, London, GB.
Pouillot et al., "Genetically Engineered Virulent Phage Banks in the Detection and Control of Emergent Pathogenic Bacteria" Biosecurity and Bioterrorism: Biodefense Strategy, Practice, and Science 8(2):155-169 (2010).
Kenneth Todar ., "Bacteriophage (p. 1) The Bacteriophages" Todar's Online Textbook of Bacteriology, downloaded from: http://textbookofbacteriology.net/phage.html, Jul. 24, 2015.
Desplats et al., "The diversity and evolution of the T4-type bacteriophages" Research in Microbiology, 154:259-267 (2003).

* cited by examiner

*Primary Examiner* — Maria Leavitt
(74) *Attorney, Agent, or Firm* — Browdy and Neimark, PLLC

(57) ABSTRACT

The invention relates to a method for obtaining a variety of recombinant bacteriophages in which the screening proteins have been modified by the insertion in their genetic sequence of randomly produced oligonucleotides, and to bacteriophages banks that can be obtained according to said method.

9 Claims, 8 Drawing Sheets

Figure 1:
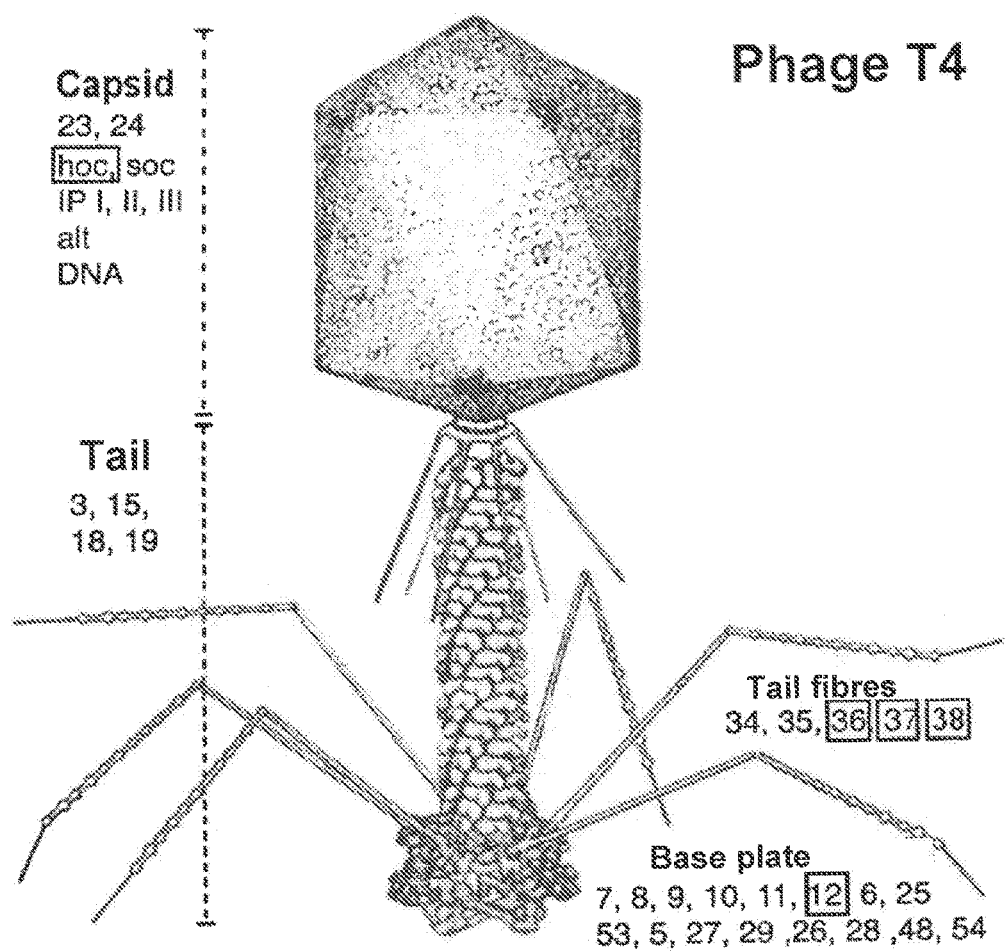

```
  1  MSNNTYQHVSNESRYVKEDPTDTNFPHEITDVHAAIAAISPAGVNGVPDASSTPKGLLFI  60
     MSNNTYQHVSNES YV+EDPT +NF   IT+V AA+A+IS  GV GVPDAS    KG++ +
  1  MSNNTYQRVSNESVYVEFDPTGSNEDSSITNVQAALASISAYGVKGVPDASEAEKGVIQL  60

61  PTEQEVIDGTNNTKAVTPATLATRLSYPNATETVYGLTRYSTNDEAIAGVNNESSITPAK  120
     +TEQEV+DG N+TKAVTPATL  RL  Y+NA+ET  YG+T+Y+T  +EAIAG  +  SITP K
 61  ATEQEVLDGFNSTKAVTPATLNARLQYPNASETQYGVTKYATQEEAIAGTLDTVSITPLK  120

121  FTVALNNAFETRVSTESSNGVIKISSLPQALAGADDTTAMTPLKTQQLAIKLIAQIAPSE  180
     ++N F TR STE++NGVISI++   ALAG+D+TTAMTPLKTQQLAI+LI+QIAP+
121  LKQFIDNTFSTRYSTETTNGVIKIAPQTAALAGSDDTTAMTPLKTQQLAIKLISQIAPNN  180

181  TTATESDQGVVQLATVAQVRQGTLREGYAISPYTFMNSSSTEEYKGVIKLGTQSEVNSNN  240
     +A+ES GVV+LATVAQ RQGTLREGYAISPYTFMNS +T+EYKGVI+LGTQ+E+NSN
181  DPASESITGVVRLATVAQTRQGTLREGYAISPYTFMNSVATQEYKGVIRLGTQAEINSNL  240

241  ASVAVTGATLNGRGSTTSMRGVVKLTTTAGSQSGGDASSALAWNADVIQQRGGQIIYGTL  300
         VAVTG TLNGRG+T SMRGVVKLTT AG   GD+S ALAWNADVI  RGGQ I G+L
241  GDVAVTGETLNGRGATGSMRGVVKLTTQAGVAPEGDSSGALAWNADVINTRGGQTINGSL  300

301  RIEDTFTIANGGANITGTVRMTGG-YIQGN--IV-QMF  DRTIPVGAIMMWAADSLPSDA  358
     ++     ANG       GG + G+ + T        +PVG I M+A DS P
301  NLD--HLTANG--------IWSRGGMWKNG  FVFRTK  ERVPVGTIQMFAGDSAP-PG  350

359  WR+     ASDCPLYASRIGTRYGONPSNPGL      FVRGSCRGSHLTNPNVNGND  418
     W               P Y + +GTR+GG+ +NPG+           FVRG+G GSH+ N   G D
351  WVL    GDQFPDYRUVVGTREGGDWNPGT       FVRGAGTGSHILNH--RGQD  408

419  QF   VGCTGGYVGEVQIQQMS IKHAC   GEHDDLGA-FGNTRRSNFVGTRKGLDW  477
     +      +KL VGC G +VG VQ QQMS  +HA+   GE    A FG +   ++GTRK  DW
409  GY     VGCDGMRVGSVQAQQMS LIKIA    GEFQRSEAPFGASVYQGYLGTRKYSDW  469

478  DNRSYFTNDGYEIDPESQRNSKYTLNRPELIGNETRPWNISLEXTKV       525
     DN SYFTNDG+E+      R++  TLNP  LIG ETRPWNISL  IK+
469  DNASYFTNDGFELG--GHRDATGTLNREGLIGYETRPWNISLM III      514
```

Fig. 5

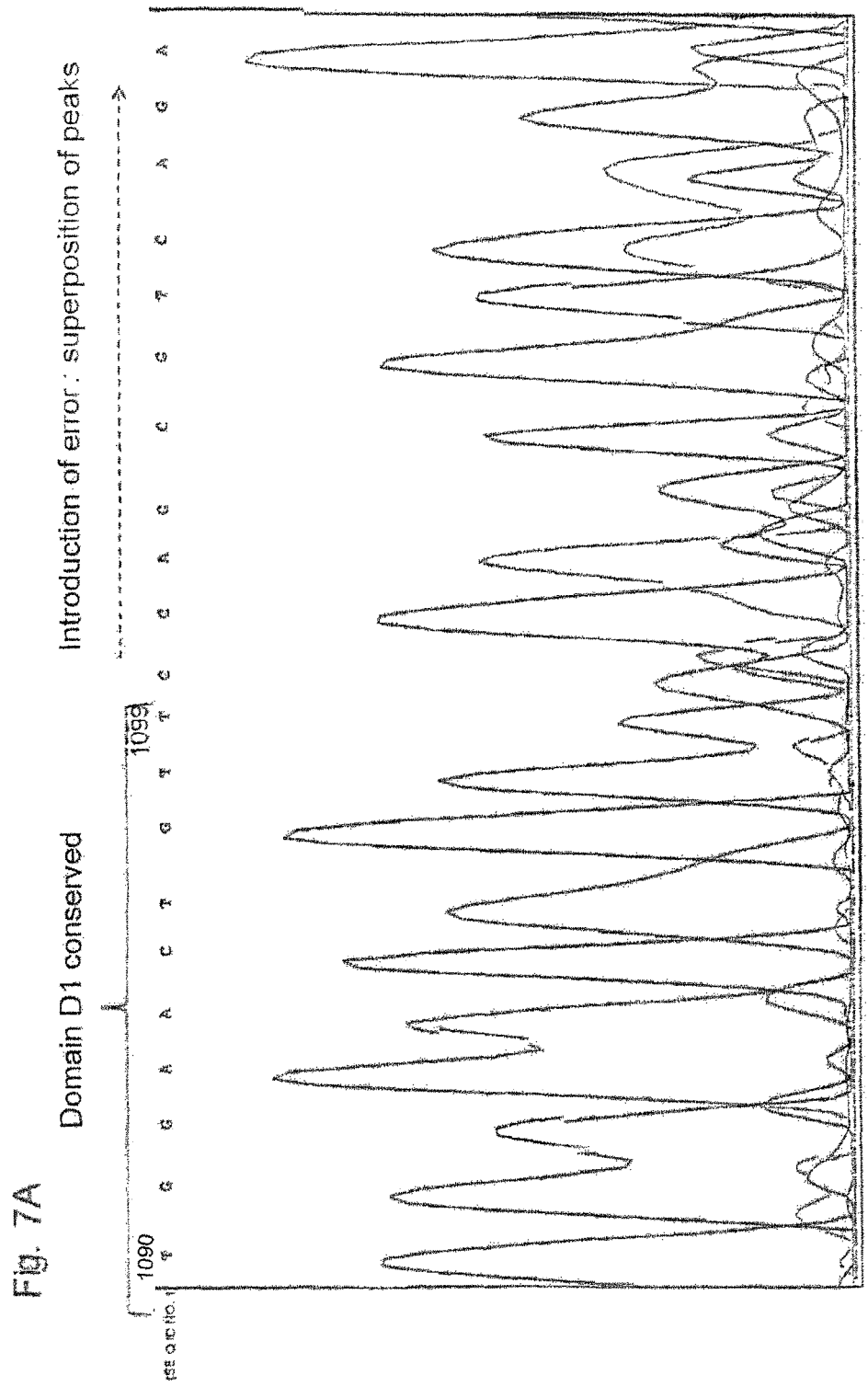

METHOD FOR THE PREPARATION OF MODIFIED BACTERIOPHAGES BY INSERTION OF RANDOM SEQUENCES IN THE TARGETING PROTEINS OF SAID BACTERIOPHAGES

The present invention relates to a method of obtaining a diversity of recombinant bacteriophages whose targeting proteins have been randomly modified, as well as bacteriophage banks that can be obtained by said method.

The bacteriophages are viruses capable of infecting bacteria specifically and of replicating therein. Their existence was demonstrated at the beginning of the XXth century by the Briton Frederick Twort and the Quebecker Felix d'Herelle.

The bacteriophages occupy all the ecological niches where there are bacteria. They occur in two main forms: the lysogenic form, by which they can remain quiescent inside their host, or else in lytic form, when they replicate actively with lysis of the bacterial cell. The lytic form causes the bacteriophages to be released in large numbers in the environment in an infectious form.

In order to maintain their infectious character with respect to their hosts, which sometimes undergo rapid mutations, the bacteriophages must constantly evolve. Accordingly, they naturally have a high degree of specialization for the bacterial species that they parasitize and are very diversified.

Since their discovery, the bacteriophages were regarded as a means of combating bacterial infections, well before the era of antibiotics.

Thus, the procedure consisting of identifying bacteriophages in nature that are specific to a pathogenic bacterium in order to treat patients infected with this bacterium was developed in Russia and in the countries of the former Soviet bloc during the first half of the XXth century.

However, antibiotics, which are generally of a broader spectrum, found general application on a massive scale in the second half of the XXth century, without all the possibilities offered by bacteriophages having been exploited.

Today, faced with the appearance of bacterial strains that are multiresistant to antibiotics, and in view of the difficulties encountered by the scientific community in developing new antibiotics, the bacteriophages are arousing renewed interest for the treatment of bacterial infections that are difficult to eradicate, in particular in the case of nosocomial contaminations [Thiel, K., *Nature Biotechnology*, 2004, 22:31-36].

However, certain difficulties still persist in the use of bacteriophages, in particular from the fact that bacteria can evade the bacteriophages by masking or modifying the constituent elements of their outer wall.

The replication cycle of the bacteriophages in fact requires a step of recognition and of adhesion of the bacteriophage to the wall of the host bacterium, which determines whether it is possible for the bacteriophage to infect the bacterium, i.e. to inject the genetic material contained in its capsid inside the cytoplasm of the bacterium.

Bacteriophage T4, for example, is a bacteriophage that infects bacteria of the *Escherichia coli* type, has a replication cycle which lasts about 30 minutes at 37° C. This replication cycle begins immediately after recognition of the host bacterium by the bacteriophage, by the stage of absorption and penetration. It is reflected in the immediate cessation of expression of the genes of the host bacterium, synthesis of the enzymes necessary to the replication of the bacteriophage, 5 minutes after infection, then replication of the DNA (starting after 10 minutes) and formation of the virus (starting after 12 minutes). The replication cycle leads to bursting of the bacterium (after 30 minutes) and release to the environment of about fifty bacteriophages per lysed bacterium.

Figure 3:
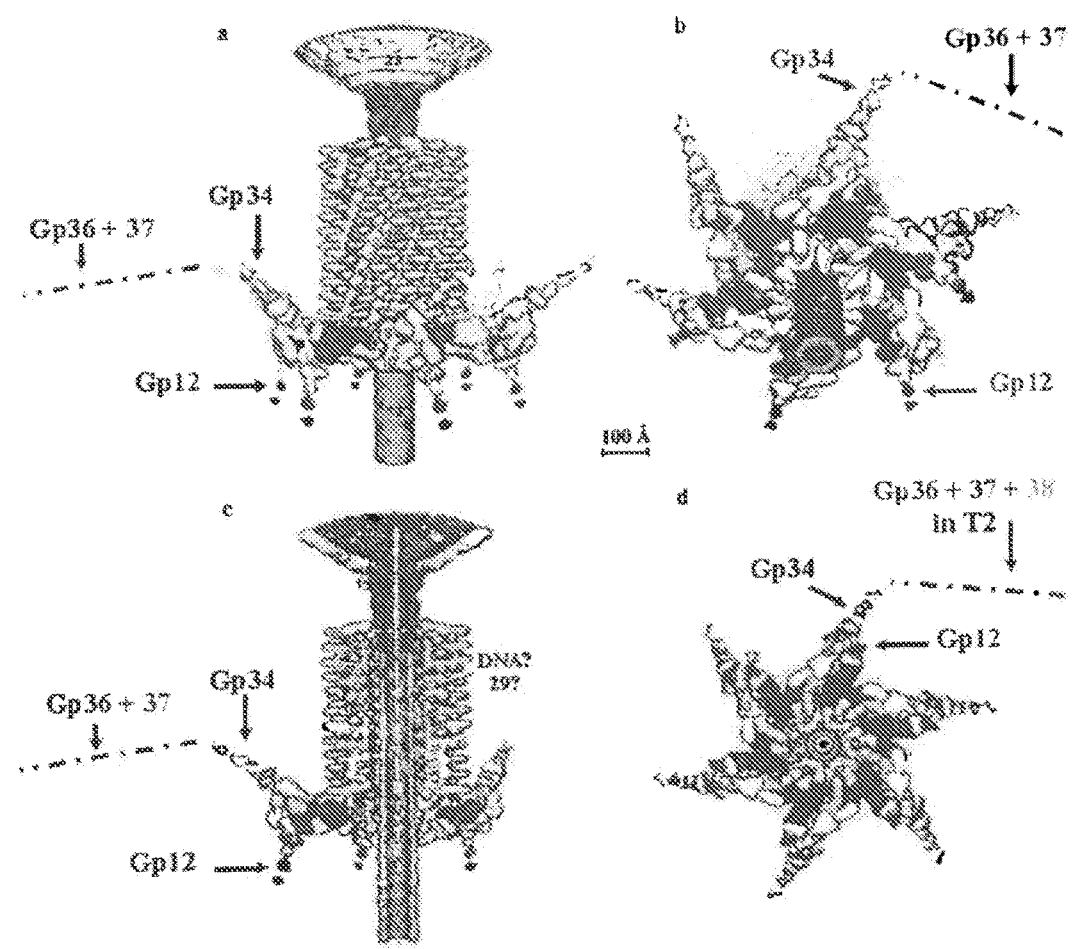

Adhesion to the bacterium is essentially provided by the proteins of the baseplate serving as anchoring for the bacteriophage, and recognition is provided more particularly by proteins forming the peripheral filaments, called "tail fibres". Nevertheless, the tail-fibre and baseplate proteins can be involved together in recognition and in adhesion of the bacteriophage to the bacterial wall. All of these so-called "targeting" proteins are represented in FIGS. 1 and 3 of the present application.

Among the proteins involved in this recognition or adhesion in bacteriophage T4, we may mention more particularly glycoproteins GP12 of the baseplate, and glycoproteins GP36, GP37 and GP38 of the tail fibres.

In order to limit the emergence of bacteria that are resistant to the recognition system of the bacteriophages, generally the simultaneous use of different forms of bacteriophages capable of targeting one and the same bacterium is proposed.

These bacteriophages are found in nature or are obtained from collections, together forming what is known as "a cocktail of bacteriophages".

However, for the development of these cocktails of bacteriophages the bacteriophages of which they are composed should be selected individually and rigorously, in particular ensuring that these bacteriophages are lytic and not lysogenic or partially lysogenic, as is often the case with bacteriophages obtained from the natural environment.

The need to test the bacteriophages individually to be certain of their real efficacy makes the development of the cocktails of bacteriophages long and arduous, especially as a different cocktail must be provided for each bacterium considered.

Application WO 01/51066 describes such a preparation of bacteriophages comprising six different bacteriophages used as a preservative of fresh foodstuffs for destroying the bacterium *Listeria monocytogenes*, which is responsible for listeriosis. This natural preparation is packaged in an atomizer for spraying on meat or on dairy products. It is harmless to humans, animals or plants, as the bacteriophages can only infect bacteria of the genus *Listeria* and not the cells of multicellular organisms.

To overcome the problems posed by the selection of natural bacteriophages, a method is proposed in application WO 06/066224 for obtaining bacteriophages whose targeting proteins are modified in order to specifically target a given virulence factor. The virulence factors are molecules described as being necessary for the bacterium to develop an infection. These molecules are regarded as stable elements, less susceptible to variation in the course of infection than the elements of external structures, such as lipopolysaccharides for example. The method described proposes selecting a protein originating from a natural bacteriophage (for example GP37 of bacteriophage T4) capable of recognizing a virulence factor described in the literature (for example OmpC of *E. coli*), of transferring the gene encoding this protein into a lambda bacteriophage and using the lambda bacteriophage for modifying said protein. The modification of the protein comprises effecting exchanges among the various domains involved in the recognition of the virulence factor (for example the His domains of GP37). These exchanges take place by means of successive recombinations between homologous domains common to these genetic sequences, which are reflected in rearrangement of the various sequences constituting the gene, without insertion of exogenous DNA.

To obtain, by this method, a diversity of the order of $10^5$ different variants of the same protein, it is necessary to carry out a large number of successive cycles of replication of the bacteriophages in the bacterial host. In fact, it is the successive recombinations that make it possible to obtain the rearrangements among different homologous regions and therefore to generate diversity.

The lambda bacteriophages thus obtained are tested for their capacity for adhering to the virulence factor targeted. This method, which is similar to the technique of phage display, makes it possible to isolate different variants of the lambda bacteriophage capable of targeting the virulence factor, and thus provide various targeting proteins. The genes corresponding to these various targeting proteins can then be transferred into infectious bacteriophages. These bacteriophages can then constitute cocktails of bacteriophages that are active with respect to the bacterium bearing the virulence factor targeted initially.

This method represents an advance in the production of diversified bacteriophages for the development of cocktails of bacteriophages. However, it can only be employed for cultivable pathogenic bacteria for which prior identification of the virulence factors was possible.

Moreover, as with the many other methods described in the prior art based on the same principle, numerous cycles of replication are necessary to obtain recombination events between homologous domains of the proteins, in sufficient number for the bacteriophages to succeed in acquiring the ability to infect hosts different from their usual hosts. In the course of this process the bacteriophages may lose the ability to infect the host used for their replication. Therefore they are eliminated from selection and evade the experimenter.

As a result there is a considerable loss of diversity of the modified bacteriophages that can be obtained using these methods.

Moreover, generally these methods only make it possible to obtain recombinant bacteriophages whose spectrum of infection is "extended", i.e. which are capable of infecting, in addition to their initial host (generally *E. coli*) other bacterial species, which are often very similar phylogenetically (Gram-negative bacteria of the genus *Salmonella* or *Shigella*) [Masatoshi Y. et al. (2005) Alteration of tail fiber protein GP38 enables T2 phage to infect *E. coli* O157:H7, Journal of Biotechnology, 115:101-107]. The production of modified targeting proteins therefore comes up against the technical constraint according to which the production of the bacteriophages is dependent on the bacterial host in which the bacteriophage is transformed and then multiplied.

To make the application of the bacteriophages more universal, it would be useful to have at our disposal bacteriophages that are infectious to a larger number of species, for example, by creating bacteriophages whose spectrum of infectivity would be modified independently of the host bacterium required for obtaining them. Such bacteriophages could be used against new bacterial species, in particular against emergent pathogenic bacteria or those causing nosocomial infections.

To overcome the aforementioned difficulties, the present invention provides a novel method consisting of diversifying the targeting proteins of bacteriophages, by inserting randomly produced DNA sequences in their genes.

This method is designed to be used with a minimum of replication cycles in the host bacterium, or even just one.

With this method it is possible to obtain a great diversity of recombinant bacteriophages in the form of banks of ready-to-use infectious bacteriophages, which can be used for treating, for example, emergent or mutant bacteria.

The method according to the invention is described in detail below, together with the various objects that can result from it.

FIG. 1: representation of bacteriophage T4 showing the different constituent elements of the bacteriophage. The proteins considered within the scope of the present invention are shown in boxes.

Figure 2:
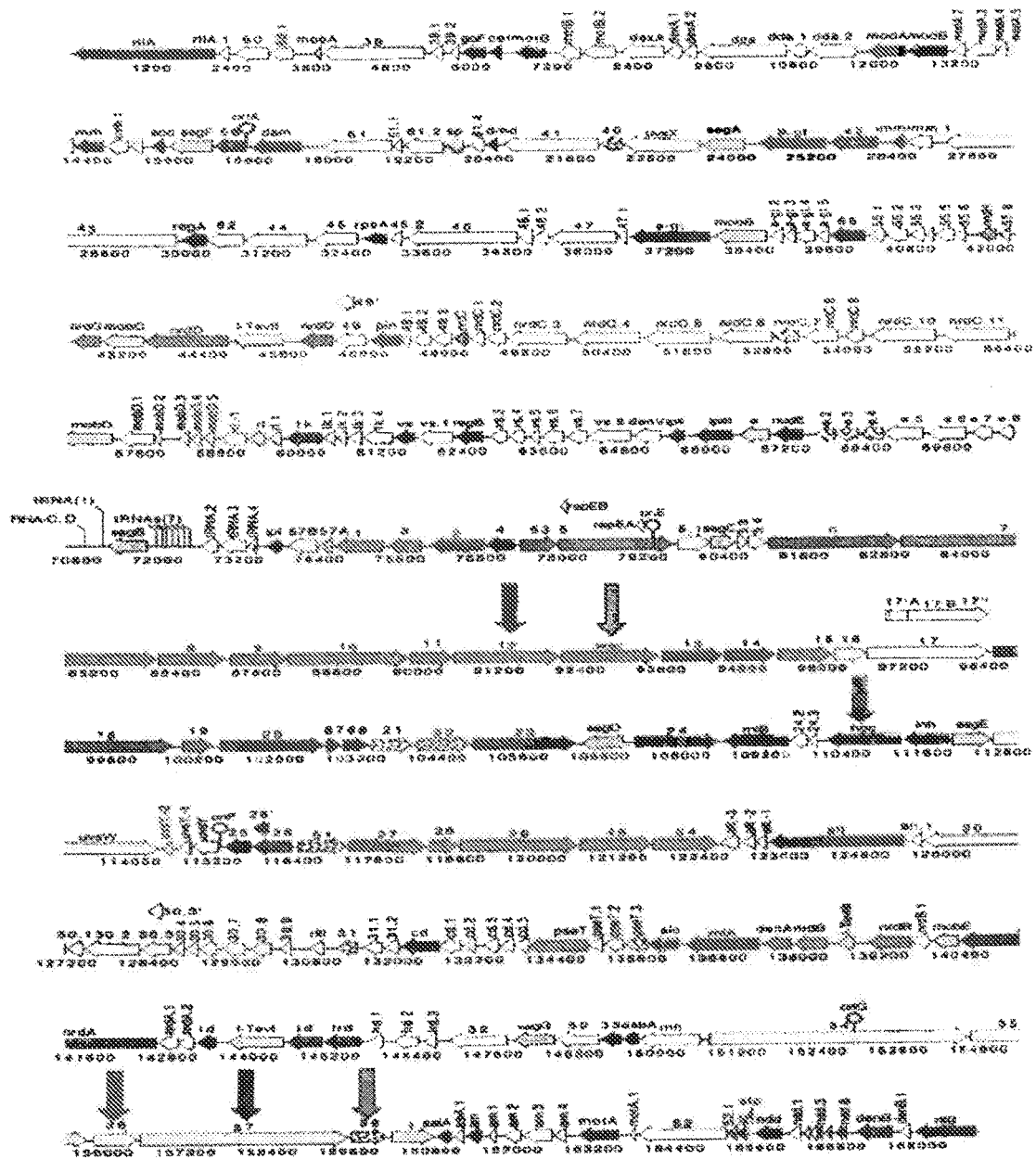

FIG. 2: representation of the complete genome of bacteriophage T4. The genes mentioned in the present application are indicated with an arrow perpendicular to the open reading frames.

FIG. 3: three-dimensional representation of the baseplate of the bacteriophage and of the tail fibres involved in recognition and adhesion of the bacteriophage to the host bacterium, making it possible to see the targeting proteins modified according to the method of the invention.

Figure 4:
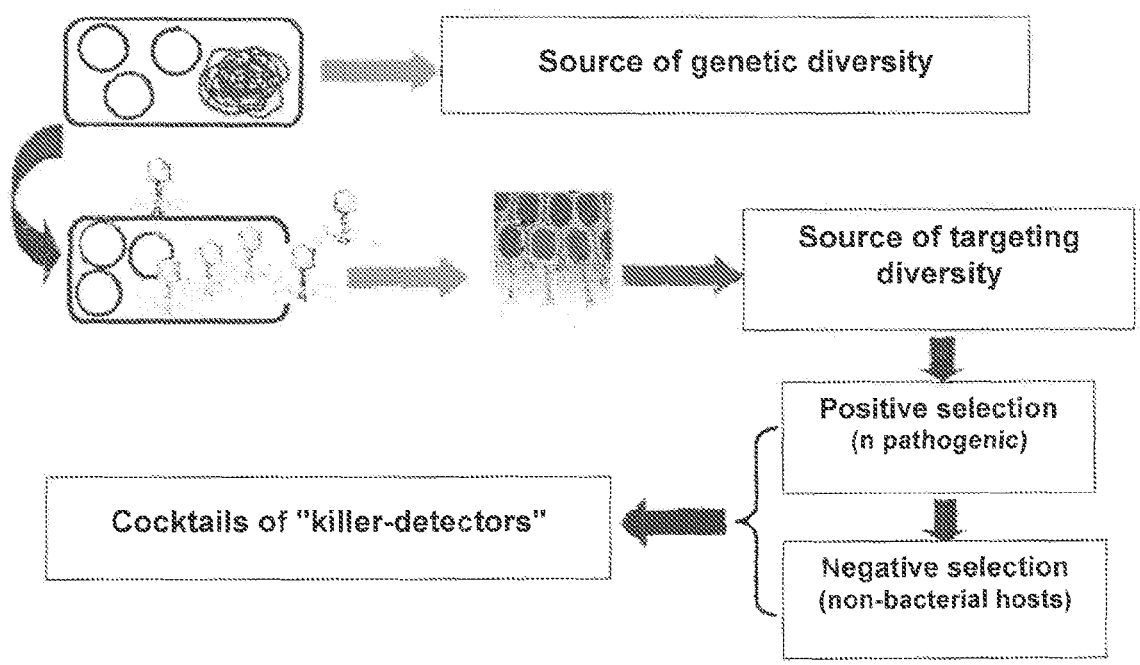

FIG. 4: schematic diagram summarizing the principle of production of a bank of recombinant bacteriophages according to the invention. The box at top left shows a host bacterium comprising 3 homologous recombination vectors for introducing oligonucleotides whose sequence is produced randomly in three genes encoding the targeting proteins of the bacteriophage. These vectors represent DNA constructs in the sense of the present invention, bearing considerable genetic diversity. After infection by a bacteriophage and homologous recombination, a large number of bacteriophages (bank of bacteriophages) having modified targeting proteins are obtained, forming "a source of targeting diversity". The bacteriophages obtained are screened with respect to potential new hosts (positive selection) in order to select bacteriophages capable of infecting said hosts. They can also be tested on non-bacterial hosts (eukaryotic cells) to ensure that they are not dangerous to humans or to animals.

FIG. 5: comparison of the polypeptide sequence of GP12 of bacteriophage T4 (top line, SEQ ID No.14), and of its homologue present in bacteriophage RB 69 (bottom line, SEQ ID No.15), according to the BLAST protocol. The amino acids common to both proteins are indicated on the intermediate line. The symbol "+" signifies that the amino acids are similar. The N-terminal portion shown in the box corresponds to the domain of these two proteins that permits anchoring of the bacteriophage on the wall of the bacterium. It is this anchoring domain that is mutated randomly and then inserted by homologous recombination in the genome of the bacteriophage according to the invention. The inner segments D1 to D4 correspond to the sequences of the protein that are conserved in the course of the method of random diversification applied by PCR according to the invention.

Figure 6:
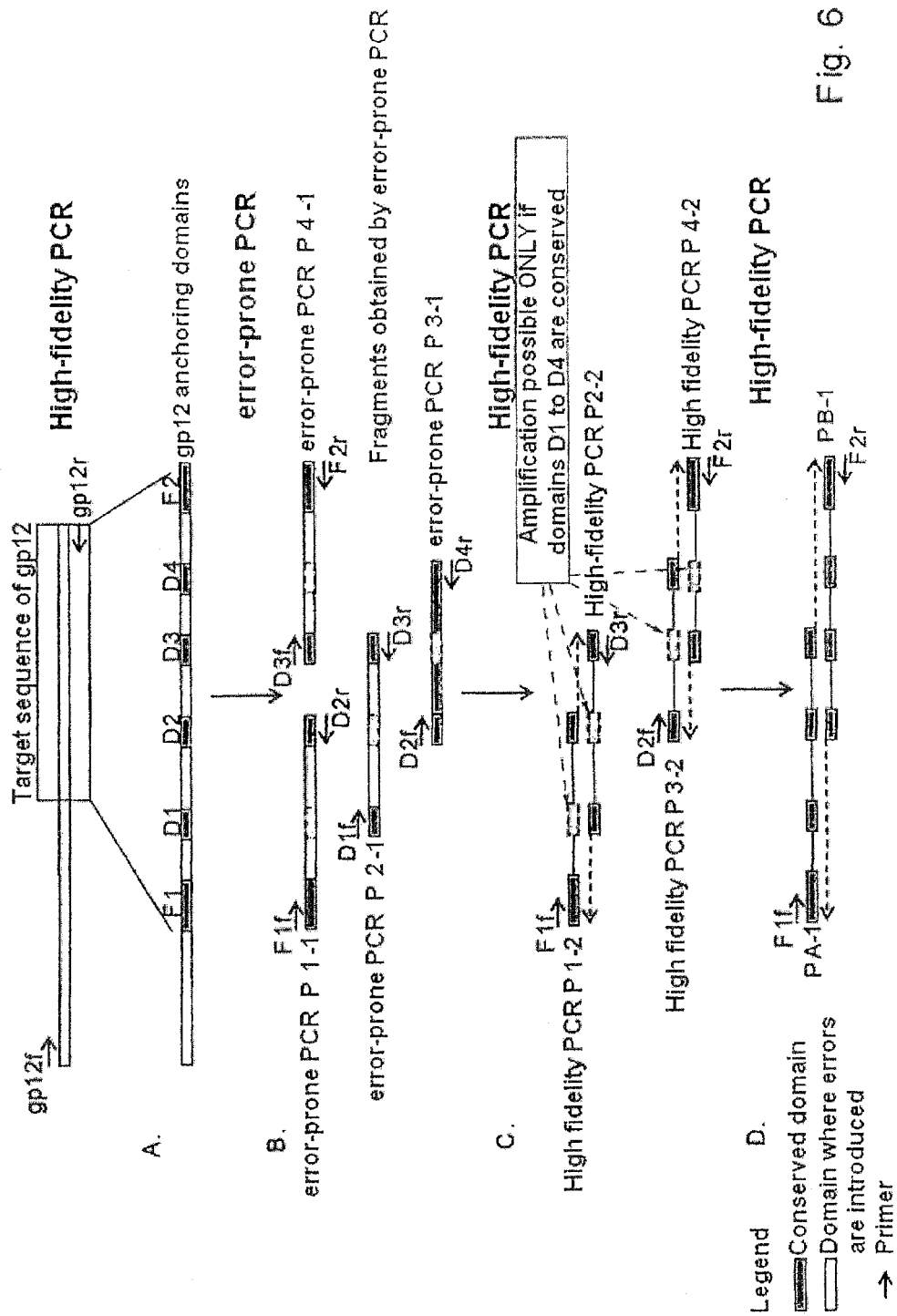

FIG. 6: diagram summarizing the steps of the PCR method employed according to the invention for obtaining, in particular, a copy of the anchoring domain of gp12 in which oligonucleotides produced randomly are inserted. The inner segments 1 to D4 whose sequence identity we wish to conserve are shown as rectangles. These domains correspond to those mentioned in FIG. 5 above. The two outer segments delimit the sequence of the anchoring domain of gp12. A: The anchoring domain of gp12 is amplified by high-fidelity PCR. B: 4 error-prone PCRs are carried out independently using the aforementioned oligonucleotides. C: The amplification products obtained in B are purified and assembled in one and the same high-fidelity PCR reaction. Said amplification products overlap so well that it is possible to assemble the various fragments, but provided that the domains D1 to D4 are sufficiently conserved to permit hybridization of the primers used. D: The PCR performed in step C results in two fragments PA-1 and PB-1, which are assembled using the primers corresponding to the outer segments of the anchoring domain of GP12. Finally, we obtain a copy of the anchoring domain of gp12 whose sequence has been modified randomly except in relation to domains D1 to D4, whose identity was conserved. The primers used in the example of application were used at each of the steps mentioned in this figure.

Figure 7B:
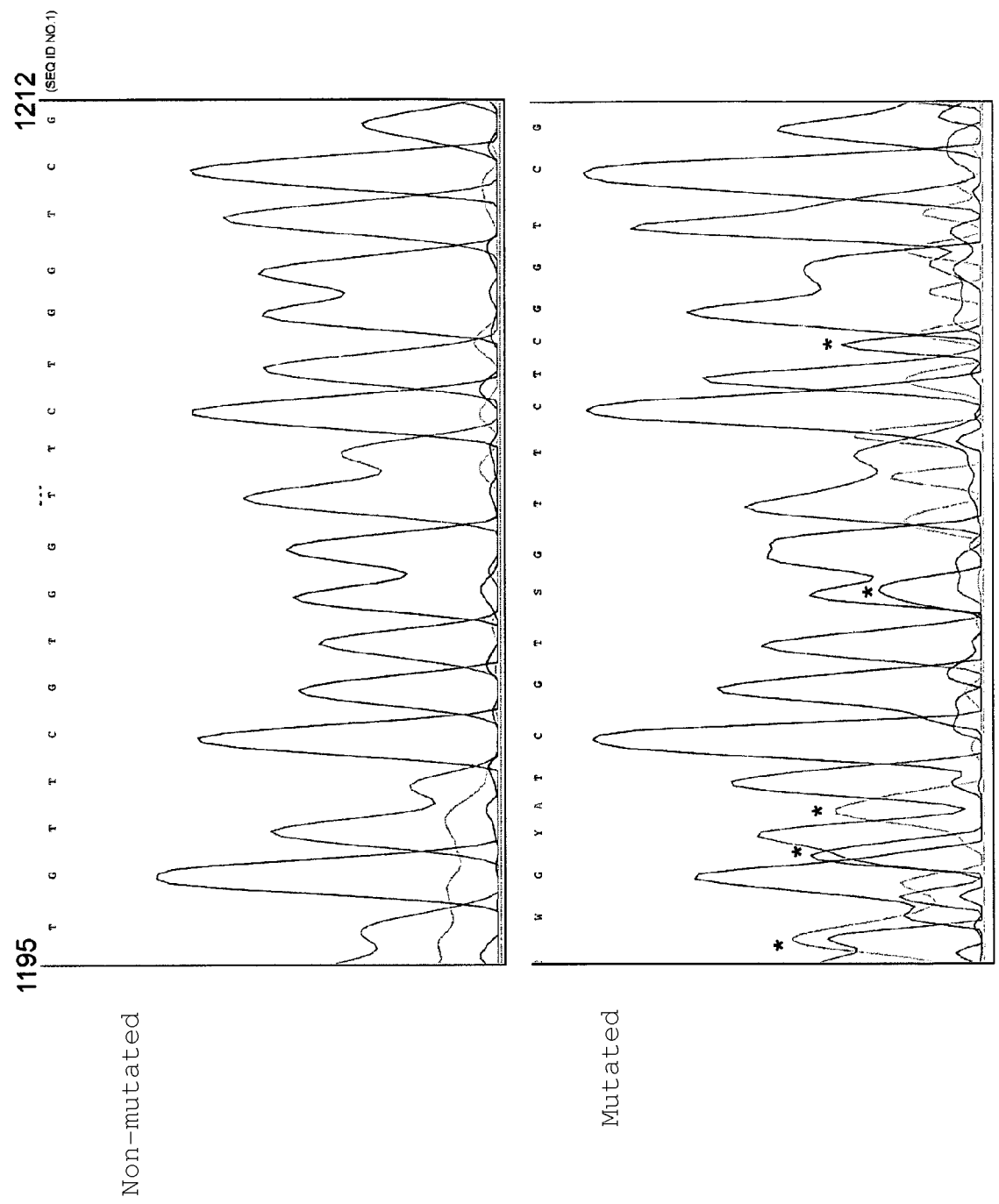

FIG. 7: Sequencing profile obtained directly on the PCR products (gp12-Mut) obtained according to the method of the invention. The profiles were established using the free ApE analysis software based on the data obtained from an automatic sequencer. FIG. 7A: sequencing of the portion of gp12 located between nucleotides 1090 and 1110 (SEQ ID NO:18). The left-hand part that is conserved corresponds to the 3' part of domain D1 (nucleotides 1090 to 1099 of SEQ ID NO:1). The right-hand part shows a superposition of peaks taking into account the random mutations that are produced in the course of the PCR method in the region located immediately downstream of D1 (nucleotides 1100 to 1110). Thus, SEQ ID NO.18 is the part of SEQ ID NO:1 corresponding to nucleotides 1090-1110 of said SEQ ID NO:1 after mutation. FIG. 7B: comparison of the sequencing performed in a non-mutated region of gp12 located between nucleotides 1195 and 1212 of SEQ ID No.1 (top) and performed for the same region on the PCR products obtained according to the method (bottom) (SEQ ID No.19). Thus, SEQ ID NO. 19 is the part of SEQ ID NO:1 corresponding to nucleotides 1195-1212 of SEQ ID NO:1 after mutation. The sequenced region is located between the conserved domains D1 and D2. The presence of superposed peaks is observed (bottom), which take account of the random insertion of nucleotides in the initial sequence of gp12.

The invention therefore relates to a method of preparation of recombinant bacteriophages, said bacteriophages taking the form of a bank of genetically modified bacteriophages.

This method comprises the following steps:

i) transforming a host bacterium by means of at least one DNA construct permitting the insertion of an oligonucleotide whose sequence has been randomly produced, in at least one gene encoding a targeting protein of a bacteriophage;

ii) infecting the bacteria transformed in step i) with said bacteriophage;

iii) placing the bacteria infected in step ii) in conditions such that the bacteriophages can replicate, and such that at least a proportion of the randomly produced oligonucleotides can be inserted in at least one gene encoding a targeting protein of said bacteriophage;

iv) harvesting the bacteriophages that replicated in the bacteria infected in step ii).

1) DNA Constructs Permitting the Insertion of a Randomly Produced Oligonucleotide According to the invention, randomly produced oligonucleotides are inserted in the genes encoding the targeting proteins of the bacteriophages. The purpose of said insertion is to introduce genetic variability into certain segments of the targeting proteins encoded by said genes. The proteins thus translated may display properties of recognition or of adhesion different from the original proteins of the bacteriophage.

The targeting proteins of the bacteriophage are defined as proteins that participate in the recognition and adhesion of the bacteriophage to the host bacterium. These proteins are preferably selected from those constituting the tail fibres or the baseplate of bacteriophage T4. A protein that is particularly suitable for the method according to the invention is protein GP12 of the baseplate, whose nucleotide sequence corresponds to SEQ ID No.1. Other preferred targeting proteins are GP36, GP37 or GP38 constituting the distal portion of the tail fibres. Of course, proteins that are homologues of those mentioned above, present in other bacteriophages, are also preferred. By "homologous sequence" is meant proteins having at least 50% identity with the latter, preferably at least 70%, more preferably at least 90%.

Preferably, the randomly produced oligonucleotides replace, by insertion, the segments of the genes of the targeting proteins corresponding to the domains of the protein involved in the functions of adhesion or recognition. Preferably, these segments correspond to variable domains, i.e. to sequences of the recognition domains that are less conserved from one species of bacteriophage to another.

Conversely, it is preferable to conserve the most constant domains of the targeting proteins because in general they are necessary for the three-dimensional structure of said proteins.

The present application gives the example of modification of protein GP12 of bacteriophage T4, which is particularly preferred according to the invention. Protein GP12 has an anchoring domain, into which it is desirable to introduce variability while maintaining the integrity of certain segments designated D (FIG. 5), said segments corresponding to conserved domains in the homologous proteins of T-type bacteriophages.

The oligonucleotides intended to be inserted in the selected domains of the proteins can be randomly produced by various techniques well known by a person skilled in the art.

"Randomly produced oligonucleotides" means, in the sense of the present invention, nucleotide sequences produced artificially containing insertions, deletions or substitutions of nucleotides, which are left to chance.

One of the aims of the invention is to introduce DNA inserts covering the greatest possible number of different combinations of nucleotides in the targeting genes without preventing the functioning of said genes.

The sequences thus produced can be introduced in the form of inserts in the genes encoding the targeting proteins of bacteriophages, for example by homologous recombination. These inserts then constitute exogenous DNA sequences, produced artificially. By way of example, for synthesizing the oligonucleotides or inserts according to the invention, it is possible to employ synthetic oligonucleotides whose sequence of natural bases A, T, C and G has been left to chance, or else oligonucleotides resulting from amplification by error-prone PCR.

According to a particular aspect of the invention, several oligonucleotides corresponding to different segments of a gene or of several genes are randomly produced in such a way that they are provided with identical 3' or 5' ends. In this way the oligonucleotides can be exchanged or substituted with one another in the modified sequence, making it possible to increase the diversity of the resultant genetic sequences.

The randomly produced oligonucleotides can also include non-natural bases, in particular "ambiguous" bases permitting the translation of a single nucleotide sequence into different polypeptides.

According to a preferred aspect of the invention, the randomly produced oligonucleotides are inserted in the genes of the bacteriophage encoding the targeting proteins by means of homologous recombination.

For this, it is necessary to employ DNA constructs that allow homologous recombination to be carried out.

Such constructs are in general derived from vectors described in the literature, well known by a person skilled in the art [Sambrook J., Russel D. W. (2001) Molecular Cloning, a Laboratory Manual, CHSL Press].

Nevertheless, to obtain DNA constructs that can be used for the purposes of the present invention, it is generally necessary to adapt the known recombination vectors by cloning in them a copy of the gene or of the part of the modified gene that we wish to introduce in the genome.

According to the invention, the genes are modified by introducing several randomly produced oligonucleotides, preferably at places corresponding to variable segments of said gene.

In this respect, in particular in the case of protein GP12 mentioned above, it is necessary according to the invention to reconstitute all or part of the gene encoding the desired targeting protein by including in it, at the desired locations, the various randomly produced oligonucleotides.

This reconstitution can be carried out conventionally by reconstituting a modified copy of the gene or of a part of said gene by cloning, i.e. by assembling the randomly produced oligonucleotides with conserved segments of the sequence in a vector. However, this step can prove very laborious, because of the sub-clonings and numerous verification steps that may be involved.

The present invention provides, in one of its particular aspects, a method that aims to facilitate the production of an insert consisting of the copy of a gene or of a part of a gene including randomly produced oligonucleotides.

This method can be applied to any nucleotide sequence for which we wish to alter certain segments selectively at random. In fact, this method can find application in numerous therapeutic areas. Its application is in effect particularly useful if we wish to modify the spectrum of activity of a protein by modifying targeted domains of its genetic sequence.

This method is applicable more particularly to the anchoring domain of gp12 in which we wish to conserve certain constant domains D1 to D4 shown in FIG. 5.

This method in particular consists of a method of PCR permitting random mutation of a nucleotide sequence S, delimited at its 5' and 3' ends by two segments F1 and F2, while preserving the identity of at least one inner segment D of said nucleotide sequence. It comprises the following steps:
  i) an error-prone PCR is performed on the whole of sequence S using primers corresponding to segments F1 and F2, by which sequence S will be mutated randomly on its entire length;
  ii) the amplification products obtained are eluted;
  iii) high-fidelity PCR is carried out starting from the amplification products eluted in step ii), using the primer pairs corresponding respectively to at least F1 and D, and F2 and D, in order to amplify at least regions F1-D and D-F2 of S mutated in step i) whose inner segment D has preserved its identity;
  iv) high-fidelity PCR is performed starting from the amplification products obtained in step iii) using the primers corresponding to F1 and F2;
  v) the PCR products obtained, whose size corresponds to that of nucleotide sequence S, are purified.

A primer according to the invention is a single-stranded nucleic acid, capable of hybridizing, partially or completely, with one of the DNA strands forming the double-stranded DNA substrate of sequence S. A primer is said to be a "sense primer" when its nucleotide chain reproduces, with the exception of some nucleotides, a part of the encoding DNA strand of S. A primer is said to be an "antisense primer" of S, when its nucleotide chain reproduces, with the exception of some nucleotides, a part of the non-encoding complementary strand of S.

When a primer is described as "corresponding to" a given segment of sequence S, this signifies that it can be sense or antisense relative to a portion of S taken in its form of double-stranded DNA molecule.

The method of PCR according to the invention involves the use, more particularly, of sense and antisense PCR primers in the manner described below and in the examples of the present application.

This method is particularly advantageous when we wish to preserve the identity of several inner segments $D_N$ of nucleotide sequence S (as is the case for protein GP12). The method thus comprises the following steps:
  i) an error-prone PCR is performed on the whole of sequence S using at least two primers of which one is sense and the other antisense respectively of segments F1 and F2, so as to amplify sequence S, introducing mutations into it randomly;
  ii) the amplification products obtained, which correspond to randomly mutated copies of S, are purified;
  iii) high-fidelity PCR is performed starting from the amplification products purified in step ii), using as sense and antisense primer pairs, respectively, at least:
    a sense primer corresponding to F1 and an antisense primer of $D_N$, in order to amplify at least region F1-$D_N$ of the mutated copies of S, and
    a sense primer corresponding to $D_N$ and an antisense primer of F2, in order to amplify at least sequence $D_N$-F2 of the mutated copies of S;
  iv) the amplification products obtained in step iii), which consist of copies of segments F1-$D_N$ and $D_N$-F2 of sequence S mutated in step i), in which the sequence of segment D has preserved its identity, are purified;
  v) high-fidelity PCR is performed starting from the amplification products obtained in step iv) using at least one pair of sense and antisense primers of F1 and F2;
  vi) the PCR products obtained in step v), which correspond to randomly mutated nucleotide sequences of said insert in which at least the sequence of segment $D_N$ has preserved its identity, are purified.

By "error-prone PCR" is meant a polymerase chain reaction carried out in conditions that do not permit faithful replication of the DNA sequences. This type of reaction can be performed using a conventional polymerase of type Taq in low-stringency conditions and in the presence of manganese salts, as described in the literature [Cadwell, R. C. et al. 1992, *Randomization of genes by PCR mutagenesis*, PCR Methods Appl., 28-33].

High-fidelity PCR is, in contrast, a polymerase chain reaction permitting amplification of a DNA matrix with a very low replication error rate. This type of reaction can be obtained by employing, for example, a Pfu type of polymerase in stringent conditions, as described in the literature [Inmis, M. A. et al., Eds., PCR Protocols: a guide to methods and applications, 1989, Academic Press].

Advantageously, the segments of the genes that we wish to diversify themselves serve as matrix for producing the oligonucleotides by error-prone PCR. The amplification products obtained according to this particular method constitute a bank of nucleotide sequences S diversified randomly whose inner domains $D_N$ have been conserved, said sequences comprising:
  the insertion of one or more randomly produced oligonucleotides; and
  sequence segments of said gene that have preserved their identity.

In general the inner segments $D_N$ preserve, according to the method of the invention, more than 50% identity relative to their original sequence in the wild-type protein, preferably more than 70%, and more preferably more than 90%, or even more than 99%, according to the PCR conditions used.

Once they are translated into protein, the nucleotide sequences contained in the aforementioned bank can result in the expression of proteins displaying a diversity of polypeptide sequences produced randomly including inner domains $D_N$ whose sequence is preserved.

These sequences can be directly cloned in expression vectors, or more preferably in homologous recombination vectors, which are available to a person skilled in the art.

It is possible, by the method described above, to modify the genome of a bacteriophage by means of diversified homologous recombination vectors including random variants of one and the same gene, preferably a gene encoding a targeting protein of a bacteriophage.

The DNA constructs according to the invention preferably comprise:
- a region permitting the duplication of said construct in a host bacterium;
- a region permitting homologous recombination in the genome of the bacteriophage in relation to a gene encoding a targeting protein, said region comprising two DNA sequences homologous to the sequences of said gene encoding a targeting protein, which delimit an insertion segment including an oligonucleotide whose sequence is produced randomly, preferably according to the method using PCR described above.

According to a preferred aspect of the invention, the region permitting homologous recombination comprises all or part of the gene encoding the targeting protein, preferably the whole of the sequence of the gene.

Preferably, this second region consists of an amplification product that can be obtained according to the method of random mutation presented above.

The DNA constructs according to the invention, considered together, make it possible for a very large number of different nucleotide sequences encoding modified targeting proteins to be integrated in the genome of the bacteriophage.

According to a preferred aspect of the invention, several genes encoding targeting proteins of the bacteriophage are mutated simultaneously by homologous recombination according to the method of the invention. To achieve such a result, the invention provides for transforming the host bacterium successively using various vectors, each targeting a different gene.

The preferred vectors permitting simultaneous modification of genes GP12, GP37 or GP38 of bacteriophage T4 according to the invention in the host bacterium *E. coli* are, for example, the vectors pACYC184 (ATCC 37033), pBAD18-K (ATCC 87397) and RR1 (ATCC 87076). Such vectors offer the advantage that they possess markers conferring resistance to various antibiotics and do not share common nucleotide sequences capable of causing recombinations between the different vectors once the latter are incorporated in the host bacterium.

2) Transformation of the Host Bacterium

A bacteriophage according to the invention is, preferably, a natural or modified, lytic bacteriophage.

Preferably, the bacteriophage used is a T-type bacteriophage, such as bacteriophages T4, T5, T6 and T7, well known by a person skilled in the art and more particularly bacteriophage T4, whose genome has been sequenced [Miller, E. S. et al., Bacteriophage T4 genome, *Microbiol Mol. Biol. Rev.*, 2003, 67(1):86-156]. The complete sequence of the genome of the bacteriophage is available in Genbank (AF 158101).

A host bacterium according to the invention is a bacterium commonly used for replicating the bacteriophage that we aim to modify. Preferably, the host bacterium is a strain that can be transformed using a DNA construct according to the invention permitting the bacteriophage to be modified by homologous recombination.

A host bacterium that is particularly suited to the T-type bacteriophages for the application of the method of the present invention is *Escherichia coli*, for example the DK8 strain (ATCC 47038).

Within the scope of the modification of T-type bacteriophages, it is advantageous to use a strain of *E. coli* transformed by means of a vector of the Mini-lambda type, derived from the lambda prophage and comprising the genes exo, bet and gam. Such a vector makes it possible, for example, to control homologous recombination as a function of the temperature at which the host bacterium is cultured and thus limit the recombination events just to the steps of replication envisaged according to the invention.

The techniques of homologous recombination used for application of the present invention are known by a person skilled in the art. They are described for example in [Poteete, A. R. et al., *FEMS Microbiol. Lett.*, 2001, 201(1):9-14; Kuzminov, A. et al. PNAS, 2001, 98(15):8298-305].

The host bacterium is therefore transformed preferably by means of a DNA construct making it possible to modify a gene encoding a bacteriophage targeting protein, comprising an insert corresponding to a randomly mutated copy of all or part of the gene encoding a targeting protein.

This insert is, preferably, produced by the method of PCR described previously.

The step of transformation of the host bacterium according to the method of the invention can take place once or more than once. When several vectors are used for modifying different genes of targeting proteins, it is advantageous to proceed sequentially, i.e. by introducing the vectors one after another. It is then possible to conserve the bacteria transformed at each step. In this way it is always possible to go back to the preceding step to reintroduce a new vector in place of that introduced last. Numerous combinations of vectors can thus be tested without having to reintroduce all the vectors in the host bacterium.

After the transformation step, we have at our disposal one or more banks of host bacteria transformed using one or more of the constructs according to the invention.

Each of the bacteria in this bank potentially contains a construct capable of transforming, by homologous recombination, one or more of the targeting proteins of the bacteriophage differently.

One object of the present invention therefore consists of a bank of host bacteria transformed by means of the DNA constructs described above, which can be infected by a bacteriophage.

Such a bank of host bacteria offers the advantage that it can be multiplied and stored. It constitutes a renewable intermediate product that can be used for the production of the recombinant bacteriophages described below.

3) Infection and Replication of the Bacteriophage in the Transformed Host Bacteria The step of infection of the host bacteria by the selected bacteriophage does not pose any particular difficulty insofar as the bacteriophage is not modified at this stage. Infection is preferably initiated during the exponential growth phase of the host bacteria, at about 30° C.

It is then in the course of the replication step of the genome of the bacteriophage in the bacterium that homologous recombination can take place between the homologous region of the gene including the randomly produced oligonucleotide and the gene present in the genome of the bacteriophage.

This replication step begins immediately after infection of the host bacteria by the bacteriophages.

According to a preferred aspect of the invention, the bacteriophages are introduced into the culture of the transformed host bacteria at the same time that a thermal shock is applied between about 40 and 45° C. This temperature is maintained for a limited time comprised between 5 and 15 minutes, preferably between 12 and 15 minutes, making it possible to activate homologous recombination. With the host bacteria preferably being transformed by means of a Mini-lambda vector making it possible to condition the homologous recombination to certain temperature conditions, in particular in the case of thermal shock, homologous recombination takes place for a time equivalent to or less than that of a replication cycle. The host bacteria are then transferred to a culture at a normal temperature of about 30° C. at which homologous recombination takes place with far more difficulty. This second period at about 30° C. lasts approximately 25 minutes, i.e. a time equivalent to a single replication cycle.

A particularly innovative aspect of the method according to the invention is the fact that the bacteriophages are harvested at the end of the second period of culture, after a single replication cycle, on average, preferably before a second replication cycle of the bacteriophages takes place.

This procedure offers the advantage of harvesting the recombinant bacteriophages before a new replication cycle in the host bacterium takes place.

This restriction to a single replication cycle means that the bacteriophages do not have time to reinfect the host bacteria for a second replication cycle. It is thus possible to harvest the modified bacteriophages that have lost the capacity to recognize or infect their host bacteria, which would otherwise be eliminated in the course of the next cycles of reinfection.

4) Banks of Recombinant Bacteriophages

The method according to the present invention makes it possible to obtain a very diversified set of recombinant bacteriophages.

These bacteriophages form a bacteriophage bank according to the invention.

A bank of recombinant bacteriophages according to the invention is therefore composed of polynucleotide variants bearing different copies of at least one gene encoding a targeting protein, said gene comprising the insertion of a randomly produced oligonucleotide sequence.

Preferably, said gene whose bacteriophages bear different copies encodes the targeting protein GP12.

The bacteriophages of which this bank is composed can also bear different copies of several genes encoding targeting proteins, said genes comprising the insertion of randomly produced oligonucleotide sequences. These different genes can be modified in the same bacteriophages or else in different bacteriophages in the same bank. Preferably, several targeting genes are modified in each bacteriophage making up the bacteriophage bank. The modified targeting proteins are preferably GP12, GP36, GP37, GP38 or proteins that are homologues of the latter. For a bacteriophage bank according to the invention to be able to cover the largest possible number of different bacteriophages, it is necessary to employ a sufficient number of transformed host bacteria, as it is this number that determines the number of bacteriophages harvested.

If this number is sufficient, a bank of bacteriophages according to the invention contains as a minimum, at least $10^3$, preferably $10^5$, more preferably $10^8$ different variants of one and the same bacteriophage, said variants differing by the sequence of at least one of their targeting proteins.

The method according to the invention thus aims, firstly, to increase the diversity of the targeting proteins expressed by the bacteriophages and prevents the elimination of the recombinant bacteriophages, in particular those that would not be replicated, or would be replicated less quickly, in the host bacterium in the course of the successive cycles of replication.

The diversity of the bacteriophages in the bank according to the invention can be demonstrated by a simple calculation of the count.

Thus, if we assume that preferably:
3 genes encoding targeting proteins are modified; by the insertion of at least 3 oligonucleotides composed of random sequences of at least 12 nucleotides; and that
1/3 of the nucleotide sequences impose a polypeptide modification in relation to the targeting proteins; and that
only 3 of the 4 bases (A, T, C, G) are capable of producing a mutation relative to the original protein;
we then obtain a minimum of $3^{24}$ possibilities of polypeptide mutations, giving a count of some $2.8 \times 10^{11}$ potentially different bacteriophages.

The present invention relates more particularly to an isolated recombinant bacteriophage, obtained from the bacteriophage bank according to the invention, capable of infecting a target bacterium and of multiplying therein.

Such a bacteriophage can be obtained by a procedure comprising the following steps:
i) introducing an oligonucleotide whose sequence is produced randomly, as described above into at least one gene encoding a targeting protein of a bacteriophage;
ii) bringing the genetically modified bacteriophages obtained according to step i) in contact with a cell whose identity is known or unknown;
iii) selecting at least one bacteriophage brought in contact in step ii), capable of infecting said cell whose identity is known or unknown.

In order to facilitate selection of the recombinant bacteriophages capable of infecting the bacteria whose identity is known or unknown according to the invention, it is advantageous to have at our disposal bacteriophages that can be detected by fluorescence or luminescence.

In this respect the bacteriophage used for infecting the host bacteria can be a bacteriophage itself previously modified, rendered fluorescent by the introduction of a gene encoding a luminescent or fluorescent protein.

According to a preferred aspect of the invention, the bacteriophage comprises a capsid protein fused with a luminescent or fluorescent protein, for example GFP (Green Fluorescent Protein).

Preferably the Hoc protein [Genbank NP 049793] of the bacteriophage capsid, or a part thereof, is fused with this luminescent or fluorescent protein. Said fusion normally has no effect on the properties of recognition and adhesion of the bacteriophage to the bacterium. The presence of a fluorescent protein makes it possible to locate bacteria which, because they are infected, harbour numerous bacteriophages. The concentration of bacteriophages there can mean that a level of fluorescence is reached that can be detected with the measuring instruments known by a person skilled in the art. These modified bacteriophages prove particularly useful for screening the infectious bacteriophages when the bacteria are cultured spread out on a solid support.

The invention also relates to a modified targeting protein extracted from a recombinant bacteriophage according to the invention or translated from the DNA obtained from said bacteriophage.

The present invention also covers any method of obtaining modified bacteriophage targeting proteins, characterized in that a recombinant bacteriophage according to the invention is employed.

5) Use of the Recombinant Bacteriophages Obtained

A bacteriophage bank according to the invention can be used for combating known or unknown bacteria. In fact, the diversity of the recombinant bacteriophages present in the bank having different targeting proteins is such that the probability that one of these bacteriophages could infect the known or unknown bacterium is significantly non-zero.

An unknown bacterium, in the sense of the present invention, is a bacterium that has not yet been characterized, or at least not sufficiently to be able to establish, for example, its antibiogram. It might be an emergent bacterium against which there is no active antibiotic, or a bacterium whose existence has not yet been established.

A bacteriophage bank according to the invention can advantageously be used preventively, against known or unknown bacteria that are able to develop on the surface of an object or in living beings.

The invention therefore also relates to a method of disinfection, characterized in that a bacteriophage bank is employed that comprises bacteriophages modified by inserting a randomly produced oligonucleotide in one or more genes encoding targeting proteins of said bacteriophage.

Another object of the invention relates to a solid or liquid composition comprising a bacteriophage bank according to the invention, for example a powder that can be sprayed on a surface that we wish to make bacteria-free.

A preferred application consists of treating air conditioners, in particular air cooling systems, by means of the bacteriophage banks according to the invention.

Such a composition can also be used as a medicinal product, in particular for preventing or treating bacterial infections and more particularly for treating respiratory-tract or skin disorders.

A recombinant bacteriophage according to the invention, which is identified as capable of infecting a given bacterium, can be used on its own in one of the applications described above.

According to a preferred aspect of the invention, a recombinant bacteriophage according to the invention can be used as a reference bacteriophage for detecting and/or identifying the known or unknown bacterium that it is capable of infecting.

A reference bacteriophage, in the sense of the invention, is a bacteriophage that has been rendered capable of targeting a given type of bacterium, so that it can serve as a tool for detection or diagnosis.

The recombinant bacteriophages according to the invention are in general obtained using laboratory strains of bacteria that are easy to culture. They may therefore prove useful compared to bacteria which, in contrast, are difficult to culture in laboratory conditions.

A recombinant bacteriophage according to the invention can therefore be employed in methods of diagnosis, for example methods comprising bringing said bacteriophage in contact with samples obtained from patients in whom a bacterial infection needs to be investigated.

According to a preferred aspect, the bacteriophages are fluorescent or luminescent, permitting real-time monitoring of the development of an infection, in particular because the bacteria can be traced by means of their respective bacteriophages.

The uses and methods described above are particularly useful in emergency situations for detecting or combating an emergent or resistant bacterium.

The examples given below have the purpose of illustrating the invention, though without limiting its scope.

Preparation of the Sequences of Variants of Gp12, Gp37 and Gp38 of T4 Bacteriophages What follows describes the procedure used for gp12, but it can be transferred without difficulty for a person skilled in the art to the modification of other genes encoding targeting proteins according to the invention, such as gp37 and gp38.

Step 1: Preparation of the Gp12 Gene

The gp12 gene is amplified by PCR starting from the genomic DNA of T4 wild-type obtained from a concentrated culture of bacteriophage lysate (see above) using as primers gp12F 5'-TGAGTAATAATACATATCAACACG (SEQ ID No.2), and gp12R 5'-TGATTCTTTTACCTTAATTATGTAC (SEQ ID No.3).

After purification on preparative agarose gel, the PCR product (gp12A) is used as the matrix in error-prone PCR reactions with the aim of introducing point mutations and insertions in the coding region corresponding to the receptor binding domain of gp12 (see FIG. 5).

Step 2: Introduction of Random Mutations in the Receptor Binding Domain

A series of 4 nested PCR reactions (each of 40 cycles) is carried out in the presence of Mn2 so as to induce random polymerase errors.

The error-prone PCRs are carried out in a reaction volume of 100 μl, using matrices and primers at final concentrations respectively equal to 400 ng and 30 pmol, with 0.2 mM of dATP and dGTP (of each), 1 mM of dCTP and dTTP (of each), 2.5 mM of $MgCl_2$, 0.7 mM of $MnCl_2$ and 5 U of DNA-polymerase Taq (New England Biolabs, Inc.) in reaction buffer 1×. PCR is carried out at 96° C. for 2 min, with 30 cycles at 95° C. for 1 min, 56° C. for 1 min and 72° C. for 2 min, and a final extension at 72° C. for 7 min.

The first reaction (P1-1) uses as primers:

p12NF1F 5'-TCAAGGTAACCGCATCGTAAC (SEQ ID No.4)

p12NF2R 5'-AAAGACCACGCATGTCAG (SEQ ID No.5)

The second reaction (P2-1) uses as primers:

p12NF2F 5'-TGCCATGGTGGAACTGTTCA (SEQ ID No.6)

p12NF3R 5'-CACCTAATCTAGGTTTAC (SEQ ID No.7)

The third reaction (P3-1) uses as primers:

p12NF3F 5'-CTGACATGCGTGGTCTTT (SEQ ID No.8)

P12NF4R 5'-ATGTTTATGATAAGACAT (SEQ ID No.9)

The fourth reaction (P4-1) uses as primers:

p12NF4F 5'-GTAAACCTAGATTAGGTG (SEQ ID No.10)

p12NF5R 5'-TCATTCTTTTACCTTAATTAT (SEQ ID No.11)

Each of these reaction products displays a partial overlap with two other reaction products and the primers used correspond to constant domains conserved in protein gp12. These domains must be faithfully preserved in the final mutated gene structures produced. However, some of the fragments produced by the error-prone PCR reactions might well have undergone mutagenesis in these regions. In order to preserve intact domains, each of the aforementioned products must then be submitted to high-fidelity PCR reactions with the aim of selective amplification of only the fragments in which the conserved domain was retained.

Step 3: Selective Amplification of the Desired Fragments

This is effected by two series of high-fidelity PCR reactions, each comprising 25 cycles.

The high-fidelity PCRs are carried out in a reaction volume of 50 µl, using matrices and primers at final concentrations respectively equal to 250 ng and 40 pM, in buffer for pfu 1×(Tris-HCl 20 mM at pH 9.0, KCl 10 mM, MgSO$_4$ 1 mM, (NH$_4$)$_2$SO$_4$ 6 mM, 0.1% of Triton X-100, 0.1 mg/ml of SAB) with 200 µM of dNTP and 5 U of pfu polymerase (Promega). The PCR profiles are as follows: 94° C. for 20 s, 45° C. for 15 s and 72° C. for 30 s, with repetition for 20 cycles.

In the first series of reactions (P1-2 to P4-2), an aliquot (about 250 ng) of each of the aforementioned PCR products is amplified using the corresponding "F" primers (for example: p12NF1F) biotinylated at the 5' end. This is necessary for separating the desired products from the matrices that cannot be amplified (mutated conserved domains) which have practically identical lengths and cannot be separated by gel electrophoresis.

The products from each reaction are then passed through size-exclusion minicolumns (to remove the excess of primers), purified individually on streptavidin beads, washed in binding buffer, eluted, precipitated and resuspended in ddH$_2$O.

In the second series of reactions, an aliquot of the purified reaction products P1-2 is mixed with an equal quantity of reaction products P2-2. They have the priming site F2-R1 and F3-R2 in common. Consequently, the "-" strand of the products of reaction P2-2 serves as primer for the "+" strand of the products of reaction P1-2 and extension with a polymerase begins at the inner priming site F2-R1 of P1-2. Extension fails for the products of reaction P1-2 where this conserved site was mutated significantly.

Similarly, the "+" strand of the products of reaction P1-2 serves as primer for the "-" strand of the products of reaction P2-2 and extension with a polymerase begins at the inner priming site F3-R2 of P2-2. Extension fails for the products of reaction P2-2 where this conserved site was mutated significantly.

The PCR products amplified successfully (PA-1) correspond to fusion of fragments P1-2 and P2-2 in which each of the four conserved domains (F1+F2-R1+F3-R2+F4-R3) was retained in the non-mutated state.

A similar mixture is prepared from the products of reaction P3-2 and P4-2. In these reactions, successful extension is based on intact inner conserved sites F4-R3 (P3-2) and F5-R4 (P4-2) and the resultant PCR products (PA-1 and PB-1) correspond to fusion of fragments P3-2 and P4-2 in which each of the four conserved domains (F3-R2+F4-R3+F5-R4+R5) was obtained in the non-mutated state.

The products obtained are purified by preparative gel electrophoresis as the dimensions of the fused PCR products are very different from those of the individual matrices.

In order to increase the yield in this second series of PCR reactions, the extension protocol can be modified as follows:

10 cycles with only the products P1-2 and P2-2, and P3-2 and P4-2 in the reaction mixtures.

The reactions are interrupted, 50 ng of each of the primers p12NF1F and p12NF3R is added to mixture PA-1 whereas 50 ng of each of the primers p12NF3F and p12NF5R is added to mixture PB-1, then the PCR reactions are allowed to continue for 15 additional cycles.

Step 4: Reconstitution of the Mutated Anchoring Domain of Gp12

After purification, equal aliquots of the products PA-1 and PB-1 are used together in a high-fidelity PCR reaction comprising 30 cycles for the purpose of reconstituting the complete receptor binding domain of gp12 in unique fragments containing the various mutations introduced above.

In this case, as in the preceding series of reactions, products PA-1 serve as extension primers for products PB-1 and vice versa.

The final fused PCR product (gp12BD-Fu) is purified by gel electrophoresis as its dimensions are very different from those of the individual matrices.

In order to increase the yield, the extension protocol can be modified by proceeding with a reaction comprising 15 cycles with only the products P1-2 and P2-2, and P3-2 and P4-2 in the reaction mixtures. The reactions are interrupted, 50 ng of each of the primers p12NF1F and p12NF5R is added to the mixture, then the PCR reactions are allowed to continue for 15 additional cycles.

After purification, an aliquot (about 250 ng) of the reconstituted receptor binding domain of gp12 is used as matrix in a new series of four error-prone PCR reactions, followed by selective amplifications and reconstitutions of the domains in the manner described above.

However, since, at each fusion step (steps 3 and 4 above), all the possible mutations introduced individually in each sub-domain are mixed randomly in the final reconstituted receptor binding domain, there are limits as to the number of cycles of mutagenesis that can be carried out without an adverse effect on the conserved domains. In view of the necessary steps of selective amplification, it is considered that, beyond 4 successive cycles, all the mutations newly introduced will have a strong probability of an adverse effect on a conserved domain or of introduction of a reversion restoring the original, non-mutated T4 sequence.

Step 5: Reconstitution of the Modified Copy of the Gp12 Gene in its Entirety

1) Amplification of the segment of gp12 upstream of the receptor binding domain.

The gp12 gene, generated by PCR, produced above (gp12A) is used as matrix together with the primers
gp12F 5'-TGAGTAATAATACATATCAACACG (SEQ ID No.12), and
gp12AR 5'-GTTACGATGCGGTTACCTTGT (SEQ ID No.13)

This is followed by purification of the amplification products obtained on preparative agarose gel, precipitation then resuspension in ddH$_2$O.

2) Amplification of the mutated binding domain of gp12

An aliquot (about 500 ng) of the PCR product (gp12B) is used together with an equal quantity of reconstituted receptor binding domain of gp12 (gp12BD-Fu) in a high-fidelity PCR reaction. It should be noted that these two products only have an overlap of 20 bp in common. Consequently, the profile of the PCR reaction must be modified to take this into account.

Modified PCR profile: A) 30 min at 96° C. then 5 cycles of 1 min at 94° C., and 10 s at 45° C., and then B) 5 cycles of 1 min at 94° C. and 20 s at 50° C., then C) 5 cycles of 1 min at 94° C., 30 s at 50° C., and finally D) 15 cycles of 1 min at 94° C., 1 min at 55° C., and 5 seconds at 72° C.

In order to increase the yield, the reaction can be interrupted at sub-step D above and the primers gp12F and p12NF5R can be introduced into the mixture. Then the reaction is left to resume and to go to completion.

The final products (gp12-Mut) are purified on preparative agarose gel, precipitated and resuspended in ddH$_2$O until they are used.

Step 6: Verification by Sequencing of the PCR Products Gp12-Mut Obtained

The PCR products purified on agarose gel are sequenced using an automatic sequencer in order to verify that mutations have indeed been introduced randomly in gp12, while preserving domains D1 and D2 intact. Sequencing is carried out on two portions corresponding respectively to nucleotides 1090 to 1110 (FIG. 7A) and 1195 and 1212 (FIG. 7B) of gp12 (SEQ ID No.1). The sequencing profiles typically obtained are shown in FIG. 7. When their profiles are compared with those of the original sequence of gp12, it is found that numerous additional peaks are superimposed on the expected profile of gp12. These additional peaks reflect a high frequency of mutations introduced in sequence gp12 by the PCR method. These peaks are not found for domain D1, confirming that this domain has preserved its sequence identity with that of gp12.

Cloning of the Mutated Gp12 Gene in an Alternative Vector for Homologous Recombination The procedures stated above made it possible to generate, in a manner similar to gp12, the mutant genes gp37 and gp38 of T4.

The purpose of the next procedures is then to introduce these variant genes of T4 in such a way as to promote their introduction, by homologous recombination, in the genome of bacteriophage T4 so as to produce descendants of T4 having host targeting specificities different from that of the parent bacteriophage.

To this end, the mutated genes generated above must be introduced in alternative vectors (a different vector for each gene). In the present case, the vectors pACYC184, pBAD18-K and RR1 are used for cloning each of the mutated genes.

The vector chosen (for example pACYC184 for the cloning of gp12Mut) is cut at the level of site Sma I, purified and resuspended in 20 µl of ddH$_2$O and mixed with the PCR product gp12Mut in a ratio of 1:3. After ligation, the DNA is purified, resuspended in ddH$_2$O and transformed in "electrocompetent" cells DK8 (ATCC 47038). This vector bears a chloramphenicol resistance gene (Chi). Thus, after electroporation and a recovery period of 1 h, the cells are transferred to 10 ml of LB medium containing 170 µg/ml of chloramphenicol and are cultured at 30° C. for 4 h with constant aeration. Then the cells are spread on plates of LB medium+Chl and cultured overnight at 30° C. Some colonies are taken for PCR verification of the presence of the insertion segment gp12Mut and some positive colonies are cultured in LB medium+Chl for the preparation of a concentrated cell culture (DK8-p12C).

Introduction of the Mutated Genes Gp37 and Gp38 into the Host Bacterium

A fresh one-night culture of DK8-p12C is used for preparing electrocompetent cells. The vector pBAD18-K is cut at the level of site Sma I, purified and resuspended in 20 µl of ddH$_2$O and mixed with the PCR product gp37Mut in a ratio of 1:3. After ligation, the DNA is purified, resuspended in ddH$_2$O and transformed in "electrocompetent" cells DK8-p12C.

The vector used in this case bears a kanamycin resistance gene (Kan). Thus, after electroporation and a recovery period of 1 h, the cells are transferred to 10 ml of LB medium containing 170 µg/ml of chloramphenicol and 50 µg/ml of kanamycin and are cultured at 30° C. for 4 h with constant aeration. Then the cells are spread on plates of LB medium+Chl+Kan and cultured overnight at 30° C. Some colonies are taken for PCR verification of the presence of the insertion segments gp12Mut and gp37Mut and some positive colonies are cultured in LB medium+Chl+Kan for the preparation of a concentrated cell culture (DK8-p12C-p37K).

A fresh one-night culture of DK8-p12C-p37K is used for preparing electrocompetent cells. The vector RR1 is cut at the level of site Sma I, purified and resuspended in 20 µl of ddH$_2$O and mixed with the PCR product gp37Mut in a ratio of 1:3. After ligation, the DNA is purified, resuspended in ddH$_2$O and transformed in "electrocompetent" cells DK8-p12C-p37K. The vector used in this case bears an ampicillin resistance gene (Amp). Thus, after electroporation and a recovery period of 1 h, the cells are transferred to 10 ml of LB medium containing 170 µg/ml of chloramphenicol+50 µg/ml of kanamycin+60 µg/ml of ampicillin and are cultured at 30° C. for 4 h with constant aeration. Then the cells are spread on plates of LB medium+Chl+Kan+Amp and cultured overnight at 30° C. Some colonies are taken for PCR verification of the presence of the insertion segments gp12Mut, gp37Mut and gp38Mut and some positive colonies are cultured in LB medium+Chl+Kan+Amp for the preparation of a concentrated cell culture (DK8-p12C-p37K-P38A).

It now remains to construct a host capable of exhibiting an extremely effective recombination potency.

Construction of E. coli "Mini-λ" Host Bacteria

To obtain effective recombination of the donor DNA in recA$^+$ or recA$^-$ backgrounds, we prepare the host E. coli which contains a prophage λ bearing the recombination genes exo, bet and gam under the control of a temperature-sensitive repressor cl of λ. The genes exo, bet and gam can easily be activated at 42° C. and inhibited at 32° C. When the λ functions are activated for a period reduced to 5 min, the cells become more recombinogenic and absorb the linear DNA without destroying it. λ Gam inhibits attack on the linear DNA by the nuclease RecBCD of E. coli, and Exo and Beta generate recombination activity for this linear DNA. More importantly, this recombination is effective with DNA homologies limited to 30 to 50 bp at the ends of substrates consisting of linear DNA.

The oligonucleotides 5' GTATGCATGCTGGGTGTGG (MARf) (SEQ ID No.16) and 5' CGCACTCTCGATTCGTA-GAGCCTCG (MARr) (SEQ ID No.17) are used as primers for the PCR amplification of the DNA from the region attP-cro using the DNA of λ c1857 as matrix.

Once the prophage λ has been generated by PCR, one possibility consists of cloning the prophage λ in the small copy number plasmid pFN476 (ATCC86962) with selection by LacZ, for example.

The vector pFN476 is cut at the level of site Sma I (free end), purified, resuspended in 20 µl of ddH$_2$O and mixed with the PCR product of prophage λ in a ratio of 1:3. After ligation, the DNA is purified, resuspended in ddH$_2$O and transformed in "electrocompetent" cells DK8-p12C-p37K-p38A. After recovery, the cells are spread on plates of LB medium X-gal+Chl+Kan+Amp (see above) and incubated at 30° C.

Some blank colonies are selected for the PCR verification of the presence of prophage λ. A colony positive for prophage λ is then cultured overnight at 30° C. in LB medium+Chl+Kan+Amp for preparing a concentrated cell culture (DK8-T4Mut-λ) to be used in further manipulations.

At this step, the transformed hosts are inducible by λ at elevated temperature, lacZ-positive and contain copies of mutated genes gp12, gp37 and gp38 of T4 ready for homologous recombination.

Production of the Descendants of T4 Bacteriophage with Extended Host Ranges

A fresh one-night culture of cells DK8-T4Mut-λ is prepared in LB medium+Chl+Kan+Amp at 30° C.

The cultures for infection by T4 are started with a volume less than or equal to 0.05 ml of cells from a one-night culture for 10 ml of LB medium+Chl+Kan+Amp in order to guarantee that the cells move on to the exponential growth phase before adding the bacteriophage.

To improve the aeration, these cultures are multiplied in 250-ml side-branch Erlenmeyer flasks, stoppered non-hermetically, in a water bath of a shaker at 30° C.

250 ml of cells in LB medium+Chl+Kan+Amp are cultured at a density of $3\times10^8$ cells per ml at 30° C. with shaking.

Aliquots of 10 ml of cells in exponential growth are then transferred to 40 ml of LB medium+Chl+Kan+Amp preheated to 42° C. and incubated for exactly 15 min at 42° C. with constant aeration. Tryptophan is added at a concentration of 0.02 mg/ml and followed by bacteriophage T4 at a multiplicity of about 10 particles per cell. The cultures are transferred to a water bath at 30° C., leaving growth to continue for exactly 25 min.

The aim in this case is to isolate the descendants of the first round and to halt propagation before these first-generation bacteriophage descendants have had time to transform into reproducers.

Recovering the Descendants of the Bacteriophages

The cells are collected by centrifugation at 5000 rpm for 5 minutes and the supernatant is recovered, some drops of chloroform are added and the mixture is centrifuged again for 10 min at 6000 rpm. The supernatant, excluding the chloroform, is adjusted to a concentration of buffer SM 1×($MgSO_4$ 10 mM, NaCl 100 mM, 0.01% of gelatin and Tris-HCl 50 mM [pH 7.5]) using buffer concentrated 5×, and is stored at 4° C. before analysis.

The cells collected in a pellet are resuspended in 8 ml of solution of Tris-hydrochloride 0.05 M at pH 8.0 with 25% saccharose. An aliquot of 1.6 ml of lysozyme (5 mg/ml) is added and the mixture is incubated for 5 min at 0° C. An aliquot of 3.2 ml of solution of EDTA 0.2 M is added and the mixture is incubated for an additional period of 15 min at 0° C. The cell lysate is adjusted to 500 mM of Tris-HCl at pH 7.4, 100 mM of $MnCl_2$ by means of buffer concentrated 10×, equilibrated at 15° C. and incubated with 10 U of Dnase1 (Sigma) for 2 h. The mixture is then centrifuged at 6000 rpm for 10 min. The clear supernatant is cautiously removed, adjusted to a concentration of buffer SM 1× and stored as described previously.

Verification of the Extensions of the Host Ranges

Cultures of pathogenic bacterial strains (*Yersinia* sp., *Salmonella* sp., *E. coli* O157 H7, *Enterobacter sakazakii*, etc.) are prepared.

Aliquots of 3 ml are then infected with 1 ml of concentrated culture of the descendants and incubated at 30° C. with stirring. The turbidity of the culture is determined by colorimetry immediately after infection and then every 60 min. A significant drop in culture turbidity in a time of 5 hours indicates that the particles capable of infecting the test host were present in the recombinant descendants of T4. Some drops of chloroform are added to the culture or cultures, which causes a clear decrease in turbidity, and the cultures are then centrifuged at 5000 rpm for 5 min.

The supernatant is recovered and used as infectious substance for the production of particles of bacteriophages dedicated to the bacterium tested, which in nature, cannot be attacked by the wild-type bacteriophage T4.

The invention claimed is:

1. A method for the preparation of a bank of genetically modified T-type bacteriophages comprising:
   a) providing a T-type bacteriophage comprising a gene that encodes a target protein that is involved in recognition and in adhesion of the bacteriophage to the bacterial wall of a host bacterium as the first step of the infection of the host bacterium said target protein comprising variable domains and conserved domains,
   b) synthesizing a set of randomly produced DNA sequences by PCR for insertion into the gene encoding said target protein, said synthesizing steps comprising:
      i) performing an error prone PCR reaction of the whole target nucleotide sequence (S), wherein said sequence is delimited at its 5' and 3' ends by two outer segments F1 and F2, using at least two primers, one of said primers is a sense strand and the other an antisense strand of segments F1 and F2, respectively, so as to amplify sequence S on its entire length comprising at least N inner constant domain ($D_N$) and to introduce random mutations;
      ii) purifying the amplification products obtained in stage i);
      iii) performing a high-fidelity PCR reaction starting from the amplification products purified in stage ii), using as sense and antisense primer pairs at least:
      a sense primer corresponding to F1 and an antisense primer of $D_N$, to amplify region F1-$D_N$ of S and preserve the identity of inner segment $D_N$, and an antisense primer corresponding to F2 and a sense primer corresponding to $D_{N-1}$, to amplify region $D_{N-1}$-$_{F2}$ of S and preserve the identity of inner segment $D_{N-1}$, wherein the primers corresponding to segment $D_N$ and $D_{N-1}$ hybridize with the whole of $D_N$ and $D_{N-1}$, respectively;
      iv) purifying the amplification products obtained in stage iii);
      v) performing a high-fidelity PCR reaction starting from the amplification products purified in stage iv), using at least one pair of sense and antisense primers F1 and F2; and
      vi) purifying the amplification products obtained in stage v), wherein the identity of the at least N inner domains $D_N$ and $D_{N-1}$ of said nucleotide sequence S are preserved,
   c) transforming the host bacterium using homologous recombination oligonucleotide constructs comprising said set of randomly produced DNA sequences,
   d) infecting the bacterium transformed in stage c) with said bacteriophage;
   e) allowing the bacteriophage to replicate within the transformed host bacterium, thus causing that at least a proportion of the randomly produced DNA sequences to be inserted by homologous recombination into the gene encoding for the target protein of said bacteriophage; and
   f) harvesting the bacteriophages that replicated in the bacteria infected in stage e), on an average, after a single cycle of replication of the bacteriophage in the transformed host bacterium and before a second replication takes place, thereby producing the bank of genetically modify bacteriophages in which the target protein of bacteriophages is diversified by inserting randomly produced oligonucleotides sequences in the genes encoding the target proteins of the bacteriophage.

2. The method according to claim 1, wherein the host bacterium is the DK8 strain of *E. coli*.

3. The method according to claim 1, wherein the bacteriophage used for infecting the transformed host bacteria is a T4 bacteriophage.

4. The method according to claim 1, wherein the bacteriophage used for infecting the transformed host bacteria is a bacteriophage itself modified and made fluorescent by the introduction of a gene encoding a luminescent or fluorescent protein.

5. The method according to claim 4, wherein the bacteriophage used for infecting the transformed host bacteria is a bacteriophage having a capsid protein fused with a luminescent or fluorescent protein.

6. The method according to claim 5, wherein the luminescent or fluorescent protein is fused with the Hoc protein of the capsid of the bacteriophage or a part thereof.

7. The method according to claim 1, wherein the targeting protein is selected from the group consisting of proteins GP12, GP36, GP37, GP38, and proteins that are homologues thereof.

8. The method according to claim 1, wherein the targeting protein is GP12.

9. The method according to claim 1, wherein each member of said set of randomly produced DNA sequences inserted by homologous recombination comprises a copy of at least one gene encoding for a modified target protein, said gene comprising the insertion of a randomly produced DNA sequence.

* * * * *

SEQUENCE LISTING

```
<160> NUMBER OF SEQ ID NOS: 19

<210> SEQ ID NO 1
<211> LENGTH: 1582
<212> TYPE: DNA
<213> ORGANISM: bacteriophage T4
<220> FEATURE:
<221> NAME/KEY: misc_feature
<222> LOCATION: (1)..(1582)
<223> OTHER INFORMATION: coding sequence of gene gp12 of bacteriophage
      T4

<400> SEQUENCE: 1
gagtaataat acatatcaac acgtttctaa tgaatctcgt tatgtaaaat ttgatcctac    60
cgatacgaat tttccaccgg agattactga tgttcacgct gctatagcag ccatttctcc   120
tgctggagta aatggagttc ctgatgcatc gtcaacaaca aagggaattc tatttattcc   180
cactgaacag gaagttatag atggaactaa taataccaaa gcagttacac cagcaacgtt   240
ggcaacaaga ttatcttatc caaatgcaac tgaaactgtt tacggattaa caagatattc   300
aaccaatgat gaagccattg ccggagttaa taatgaatct tctataactc cagctaaatt   360
tactgtcgcc cttaataatg cgtttgaaac gcgagtttca actgaatcct caaatggtgt   420
tattaaaatt tcatctctac cgcaagcatt agctggtgca gatgatacta ctgcaatgac   480
tccattaaaa acacagcagt tagctattaa attaattgcg caaattgctc cttctgaaac   540
cacagctacc gaatcggacc aaggtgttgt tcaattagca acagtagcgc aggttcgtca   600
gggaacttta agagaaggct atgcaatttc tccttatacg tttatgaatt catcttctac   660
tgaagaatat aaaggcgtaa ttaaattagg aacacaatca gaagttaact cgaataatgc   720
ttctgttgcg gttactggcg caactcttaa tggtcgtggt tctacgacgt caatgagagg   780
cgtagttaaa ttaactacaa ccgccggttc acagagtgga ggcgatgctt catcagcctt   840
```

-continued

```
agcttggaat gctgacgtta tccagcaaag aggtggtcaa attatctatg gaacactccg    900
cattgaagac acatttacaa tagctaatgg tggagcaaat attacgggta ccgtcagaat    960
gactggcggt tatattcaag gtaaccgcat cgtaacacaa aatgaaattg atagaactat   1020
tcctgtcgga gctattatga tgtgggccgc tgatagtctt cctagtgatg cttggcgctt   1080
ctgccatggt ggaactgttt cagcgtcaga ttgtccatta tatgcttcta gaattggaac   1140
aagatatggc ggaaacccat caaatcctgg attgcctgac atgcgtggtc tttttgttcg   1200
tggttctggt cgtggttctc acttaacaaa tccaaatgtt aatggtaatg accaatttgg   1260
taaacctaga ttaggtgtag gttgtaccgg tggatatgtt ggtgaagtac agatacaaca   1320
gatgtcttat cataaacatg ctggtggatt tggtgagcat gatgatctgg gggcattcgg   1380
taatacccgt agatcaaatt ttgttggtac acgtaaagga cttgactggg ataaccgttc   1440
atacttcacc aatgacggat atgaaattga cccagaatca caacgaaatt ccaaatatac   1500
attaaatcgt cctgaattaa ttggaaatga aacacgtcca tggaacattt ctttaaacta   1560
cataattaag gtaaaagaat ga                                            1582
```

```
<210> SEQ ID NO 2
<211> LENGTH: 24
<212> TYPE: DNA
<213> ORGANISM: Artificial Sequence
<220> FEATURE:
<223> OTHER INFORMATION: gp12F primer for amplification of gene gp12 of
      bacteriophage T4
<220> FEATURE:
<221> NAME/KEY: misc_feature
<223> OTHER INFORMATION: Synthetic

<400> SEQUENCE: 2
tgagtaataa tacatatcaa cacg                                            24

<210> SEQ ID NO 3
<211> LENGTH: 25
<212> TYPE: DNA
<213> ORGANISM: Artificial Sequence
<220> FEATURE:
<223> OTHER INFORMATION: gp12R primer for amplification of gene gp12 of
      bacteriophage T4
<220> FEATURE:
<221> NAME/KEY: misc_feature
<223> OTHER INFORMATION: Synthetic

<400> SEQUENCE: 3
tgattctttt accttaatta tgtac                                           25

<210> SEQ ID NO 4
<211> LENGTH: 21
<212> TYPE: DNA
<213> ORGANISM: Artificial Sequence
<220> FEATURE:
<223> OTHER INFORMATION: P12NF1F primer of anchoring domain of gene gp12
      of bacteriophage T4
<220> FEATURE:
<221> NAME/KEY: misc_feature
<223> OTHER INFORMATION: Synthetic

<400> SEQUENCE: 4
tcaaggtaac cgcatcgtaa c                                               21

<210> SEQ ID NO 5
<211> LENGTH: 18
<212> TYPE: DNA
```

<213> ORGANISM: Artificial Sequence
<220> FEATURE:
<223> OTHER INFORMATION: P12NF2R primer of anchoring domain of gene gp12 of bacteriophage T4
<220> FEATURE:
<221> NAME/KEY: misc_feature
<223> OTHER INFORMATION: Synthetic

<400> SEQUENCE: 5
aaagaccacg catgtcag                                                 18

<210> SEQ ID NO 6
<211> LENGTH: 20
<212> TYPE: DNA
<213> ORGANISM: Artificial Sequence
<220> FEATURE:
<223> OTHER INFORMATION: P12NF2F primer of anchoring domain of gene gp12 of bacteriophage T4
<220> FEATURE:
<221> NAME/KEY: misc_feature
<223> OTHER INFORMATION: Synthetic

<400> SEQUENCE: 6
tgccatggtg gaactgttca                                               20

<210> SEQ ID NO 7
<211> LENGTH: 18
<212> TYPE: DNA
<213> ORGANISM: Artificial Sequence
<220> FEATURE:
<223> OTHER INFORMATION: P12NF3R primer of anchoring domain of gene gp12 of bacteriophage T4
<220> FEATURE:
<221> NAME/KEY: misc_feature
<223> OTHER INFORMATION: Synthetic

<400> SEQUENCE: 7
cacctaatct aggtttac                                                 18

<210> SEQ ID NO 8
<211> LENGTH: 18
<212> TYPE: DNA
<213> ORGANISM: Artificial Sequence
<220> FEATURE:
<223> OTHER INFORMATION: P12NF3F primer of anchoring domain of gene gp12 of bacteriophage T4
<220> FEATURE:
<221> NAME/KEY: misc_feature
<223> OTHER INFORMATION: Synthetic

<400> SEQUENCE: 8
ctgacatgcg tggtcttt                                                 18

<210> SEQ ID NO 9
<211> LENGTH: 18
<212> TYPE: DNA
<213> ORGANISM: Artificial Sequence
<220> FEATURE:
<223> OTHER INFORMATION: P12NF4R primer of anchoring domain of gene gp12 of bacteriophage T4
<220> FEATURE:
<221> NAME/KEY: misc_feature
<223> OTHER INFORMATION: Synthetic

<400> SEQUENCE: 9
atgtttatga taagacat                                                 18

<210> SEQ ID NO 10
<211> LENGTH: 18

<212> TYPE: DNA
<213> ORGANISM: Artificial Sequence
<220> FEATURE:
<223> OTHER INFORMATION: P12NF4F primer of anchoring domain of gene gp12
of bacteriophage T4
<220> FEATURE:
<221> NAME/KEY: misc_feature
<223> OTHER INFORMATION: Synthetic

<400> SEQUENCE: 10
gtaaacctag attaggtg                                                   18

<210> SEQ ID NO 11
<211> LENGTH: 21
<212> TYPE: DNA
<213> ORGANISM: Artificial Sequence
<220> FEATURE:
<223> OTHER INFORMATION: P12NF5R primer of anchoring domain of gene gp12
of bacteriophage T4
<220> FEATURE:
<221> NAME/KEY: misc_feature
<223> OTHER INFORMATION: Synthetic

<400> SEQUENCE: 11 tcattcttttt accttaatta t                                              21

<210> SEQ ID NO 12
<211> LENGTH: 24
<212> TYPE: DNA
<213> ORGANISM: Artificial Sequence
<220> FEATURE:
<223> OTHER INFORMATION: gp12F primer for amplification of gene gp12 of
bacteriophage T4
<220> FEATURE:
<221> NAME/KEY: misc_feature
<223> OTHER INFORMATION: Synthetic

<400> SEQUENCE: 12
tgagtaataa tacatatcaa cacg                                            24

<210> SEQ ID NO 13
<211> LENGTH: 21
<212> TYPE: DNA
<213> ORGANISM: Artificial Sequence
<220> FEATURE:
<223> OTHER INFORMATION: gp12AR primer for amplification of gene gp12 of
bacteriophage T4
<220> FEATURE:
<221> NAME/KEY: misc_feature
<223> OTHER INFORMATION: Synthetic

<400> SEQUENCE: 13
gttacgatgc ggttaccttg t                                               21

<210> SEQ ID NO 14
<211> LENGTH: 525
<212> TYPE: PRT
<213> ORGANISM: bacteriophage T4

<400> SEQUENCE: 14

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
            20                  25                  30

His Ala Ala Ile Ala Ala Ile Ser Pro Ala Gly Val Asn Gly Val Pro
        35                  40                  45

Asp Ala Ser Ser Thr Thr Lys Gly Ile Leu Phe Ile Pro Thr Glu Gln

-continued

```
                50                  55                  60
Glu Val Ile Asp Gly Thr Asn Asn Thr Lys Ala Val Thr Pro Ala Thr
 65                  70                  75                  80

Leu Ala Thr Arg Leu Ser Tyr Pro Asn Ala Thr Glu Thr Val Tyr Gly
                 85                  90                  95

Leu Thr Arg Tyr Ser Thr Asn Asp Glu Ala Ile Ala Gly Val Asn Asn
                100                 105                 110

Glu Ser Ser Ile Thr Pro Ala Lys Phe Thr Val Ala Leu Asn Asn Ala
                115                 120                 125

Phe Glu Thr Arg Val Ser Thr Glu Ser Ser Asn Gly Val Ile Lys Ile
130                 135                 140

Ser Ser Leu Pro Gln Ala Leu Ala Gly Ala Asp Asp Thr Thr Ala Met
145                 150                 155                 160

Thr Pro Leu Lys Thr Gln Gln Leu Ala Ile Lys Leu Ile Ala Gln Ile
                165                 170                 175

Ala Pro Ser Glu Thr Thr Ala Thr Glu Ser Asp Gln Gly Val Val Gln
                180                 185                 190

Leu Ala Thr Val Ala Gln Val Arg Gln Gly Thr Leu Arg Glu Gly Tyr
                195                 200                 205

Ala Ile Ser Pro Tyr Thr Phe Met Asn Ser Ser Thr Glu Glu Tyr
                210                 215                 220

Lys Gly Val Ile Lys Leu Gly Thr Gln Ser Glu Val Asn Ser Asn Asn
225                 230                 235                 240

Ala Ser Val Ala Val Thr Gly Ala Thr Leu Asn Gly Arg Gly Ser Thr
                245                 250                 255

Thr Ser Met Arg Gly Val Val Lys Leu Thr Thr Thr Ala Gly Ser Gln
                260                 265                 270

Ser Gly Gly Asp Ala Ser Ser Ala Leu Ala Trp Asn Ala Asp Val Ile
                275                 280                 285

Gln Gln Arg Gly Gly Gln Ile Ile Tyr Gly Thr Leu Arg Ile Glu Asp
                290                 295                 300

Thr Phe Thr Ile Ala Asn Gly Ala Asn Ile Thr Gly Thr Val Arg
305                 310                 315                 320

Met Thr Gly Gly Tyr Ile Gln Gly Asn Arg Ile Val Thr Gln Asn Glu
                325                 330                 335

Ile Asp Arg Thr Ile Pro Val Gly Ala Ile Met Met Trp Ala Ala Asp
                340                 345                 350

Ser Leu Pro Ser Asp Ala Trp Arg Phe Cys His Gly Thr Val Ser
                355                 360                 365

Ala Ser Asp Cys Pro Leu Tyr Ala Ser Arg Ile Gly Thr Arg Tyr Gly
                370                 375                 380

Gly Asn Pro Ser Asn Pro Gly Leu Pro Asp Met Arg Gly Leu Phe Val
385                 390                 395                 400

Arg Gly Ser Gly Arg Gly Ser His Leu Thr Asn Pro Asn Val Asn Gly
                405                 410                 415

Asn Asp Gln Phe Gly Lys Pro Arg Leu Gly Val Gly Cys Thr Gly Gly
                420                 425                 430

Tyr Val Gly Glu Val Gln Ile Gln Gln Met Ser Tyr His Lys His Ala
                435                 440                 445

Gly Gly Phe Gly Glu His Asp Asp Leu Gly Ala Phe Gly Asn Thr Arg
                450                 455                 460

Arg Ser Asn Phe Val Gly Thr Arg Lys Gly Leu Asp Trp Asp Asn Arg
465                 470                 475                 480
```

Ser Tyr Phe Thr Asn Asp Gly Tyr Glu Ile Asp Pro Glu Ser Gln Arg
            485                 490                 495

Asn Ser Lys Tyr Thr Leu Asn Arg Pro Glu Leu Ile Gly Asn Glu Thr
            500                 505                 510

Arg Pro Trp Asn Ile Ser Leu Asn Tyr Ile Ile Lys Val
            515                 520             525

<210> SEQ ID NO 15
<211> LENGTH: 514
<212> TYPE: PRT
<213> ORGANISM: bacteriophage RB69

<400> SEQUENCE: 15

Met Ser Asn Asn Thr Tyr Gln His Val Ser Asn Glu Ser Val Tyr Val
1               5                   10                  15

Glu Phe Asp Pro Thr Gly Ser Asn Phe Asp Ser Ser Ile Thr Asn Val
            20                  25                  30

Gln Ala Ala Leu Ala Ser Ile Ser Ala Tyr Gly Val Lys Gly Val Pro
            35                  40                  45

Asp Ala Ser Glu Ala Glu Lys Gly Val Ile Gln Leu Ala Thr Glu Gln
50                  55                  60

Glu Val Leu Asp Gly Phe Asn Ser Thr Lys Ala Val Thr Pro Ala Thr
65                  70                  75                  80

Leu Asn Ala Arg Leu Gln Tyr Pro Asn Ala Ser Glu Thr Gln Tyr Gly
                85                  90                  95

Val Thr Lys Tyr Ala Thr Gln Glu Glu Ala Ile Ala Gly Thr Leu Asp
            100                 105                 110

Thr Val Ser Ile Thr Pro Leu Lys Leu Asn Gln Thr Ile Asp Asn Thr
            115                 120                 125

Phe Ser Thr Arg Tyr Ser Thr Glu Thr Thr Asn Gly Val Ile Lys Ile
        130                 135                 140

Ala Thr Gln Thr Ala Ala Leu Ala Gly Ser Asp Asp Thr Thr Ala Met
145                 150                 155                 160

Thr Pro Leu Lys Thr Gln Gln Leu Ala Ile Lys Leu Ile Ser Gln Ile
                165                 170                 175

Ala Pro Asn Asn Asp Pro Ala Ser Glu Ser Ile Thr Gly Val Val Arg
            180                 185                 190

Leu Ala Thr Val Ala Gln Thr Arg Gln Gly Thr Leu Arg Glu Gly Tyr
            195                 200                 205

Ala Ile Ser Pro Tyr Thr Phe Met Asn Ser Val Ala Thr Gln Glu Tyr
        210                 215                 220

Lys Gly Val Ile Arg Leu Gly Thr Gln Ala Glu Ile Asn Ser Asn Leu
225                 230                 235                 240

Gly Asp Val Ala Val Thr Gly Glu Thr Leu Asn Gly Arg Gly Ala Thr
                245                 250                 255

Gly Ser Met Arg Gly Val Val Lys Leu Thr Thr Gln Ala Gly Val Ala
            260                 265                 270

Pro Glu Gly Asp Ser Ser Gly Ala Leu Ala Trp Asn Ala Asp Val Ile
            275                 280                 285

Asn Thr Arg Gly Gly Gln Thr Ile Asn Gly Ser Leu Asn Leu Asp His
        290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val

```
                    325                 330                 335
Gly Thr Ile Gln Met Phe Ala Gly Asp Ser Ala Pro Pro Gly Trp Val
                340                 345                 350
Leu Cys His Gly Gly Thr Ile Ser Gly Asp Gln Phe Pro Asp Tyr Arg
            355                 360                 365
Asn Val Val Gly Thr Arg Phe Gly Gly Asp Trp Asn Asn Pro Gly Ile
        370                 375                 380
Pro Asp Met Arg Gly Ile Phe Val Arg Gly Ala Gly Thr Gly Ser His
385                 390                 395                 400
Ile Leu Asn Asn Arg Gly Gln Asp Gly Tyr Gly Lys Asp Arg Leu Gly
                405                 410                 415
Val Gly Cys Asp Gly Met His Val Gly Val Gln Ala Gln Gln Met
                420                 425                 430
Ser Tyr His Lys His Ala Gly Gly Trp Gly Glu Phe Gln Arg His Glu
            435                 440                 445
Ala Pro Phe Gly Ala Ser Val Tyr Gln Gly Tyr Leu Gly Thr Arg Lys
        450                 455                 460
Tyr Ser Asp Trp Asp Asn Ala Ser Tyr Phe Thr Asn Asp Gly Phe Glu
465                 470                 475                 480
Leu Gly Gly His Arg Asp Ala Thr Gly Thr Leu Asn Arg Glu Gly Leu
                485                 490                 495
Ile Gly Tyr Glu Thr Arg Pro Trp Asn Ile Ser Leu Asn Tyr Ile Ile
            500                 505                 510
Lys Val

<210> SEQ ID NO 16
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: Synthetic

<400> SEQUENCE: 16
gtatgcatgc tgggtgtgg                                                  19

<210> SEQ ID NO 17
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: Synthetic

<400> SEQUENCE: 17
cgcactctcg attcgtagag cctcg                                           25

<210> SEQ ID NO 18
<211> LENGTH: 21
<212> TYPE: DNA
<213> ORGANISM: Artificial Sequence
<220> FEATURE:
<223> OTHER INFORMATION: mutated sequence of SEQ ID No. 1 (1089-1110)
<220> FEATURE:
<221> NAME/KEY: misc_feature
<223> OTHER INFORMATION: Synthetic

<400> SEQUENCE: 18
```

```
tggaactgtt ccagcgtcag a                                              21

<210> SEQ ID NO 19
<211> LENGTH: 20
<212> TYPE: DNA
<213> ORGANISM: Artificial Sequence
<220> FEATURE:
<223> OTHER INFORMATION: mutated sequence of SEQ ID No. 1 (1195-1212)
<220> FEATURE:
<221> NAME/KEY: misc_feature
<223> OTHER INFORMATION: Synthetic

<400> SEQUENCE: 19
wgyatcgtsg ttctcggtcg                                                20
```